US009269907B2

(12) United States Patent
Mizuki et al.

(10) Patent No.: US 9,269,907 B2
(45) Date of Patent: Feb. 23, 2016

(54) AROMATIC AMINE DERIVATIVE AND ORGANIC ELECTROLUMINESCENCE DEVICE USING THE SAME

(75) Inventors: Yumiko Mizuki, Sodegaura (JP); Hiroyuki Saito, Sodegaura (JP); Yuichiro Kawamura, Sodegaura (JP); Hirokatsu Ito, Sodegaura (JP); Masahiro Kawamura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 19 days.

(21) Appl. No.: 13/389,514

(22) PCT Filed: Oct. 24, 2011

(86) PCT No.: PCT/JP2011/005930
§ 371 (c)(1),
(2), (4) Date: Feb. 13, 2012

(87) PCT Pub. No.: WO2012/056674
PCT Pub. Date: May 3, 2012

(65) Prior Publication Data
US 2013/0221331 A1 Aug. 29, 2013

(30) Foreign Application Priority Data

Oct. 25, 2010 (JP) ................................. 2010-238303
Jun. 15, 2011 (JP) ................................. 2011-133558

(51) Int. Cl.
| | | |
|---|---|---|
| H01L 51/50 | (2006.01) | |
| H01L 51/00 | (2006.01) | |
| C07C 255/58 | (2006.01) | |
| C07D 213/74 | (2006.01) | |
| C07F 7/08 | (2006.01) | |
| C09K 11/06 | (2006.01) | |
| H05B 33/14 | (2006.01) | |

(52) U.S. Cl.
CPC .......... *H01L 51/0067* (2013.01); *C07C 255/58* (2013.01); *C07D 213/74* (2013.01); *C07F 7/0818* (2013.01); *C09K 11/06* (2013.01); *H01L 51/0059* (2013.01); *H01L 51/0072* (2013.01); *H01L 51/0094* (2013.01); *H05B 33/14* (2013.01); *C07C 2101/08* (2013.01); *C07C 2103/18* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *H01L 51/0058* (2013.01); *H01L 51/0068* (2013.01); *H01L 51/5012* (2013.01)

(58) Field of Classification Search
None
See application file for complete search history.

(56) References Cited

U.S. PATENT DOCUMENTS

| | | | |
|---|---|---|---|
| 7,122,256 B2 | 10/2006 | Funahashi et al. | |
| 2003/0044640 A1 | 3/2003 | Funahashi et al. | |
| 2005/0238912 A1 | 10/2005 | Funahashi et al. | |
| 2008/0004445 A1* | 1/2008 | Hosokawa et al. | 546/171 |
| 2008/0203905 A1 | 8/2008 | Je et al. | |
| 2010/0072888 A1 | 3/2010 | Kim et al. | |
| 2011/0233534 A1* | 9/2011 | Mizuki et al. | 257/40 |

FOREIGN PATENT DOCUMENTS

| | | | |
|---|---|---|---|
| JP | 7-249490 | 9/1995 | |
| JP | 2000-91074 | 3/2000 | |
| JP | 2008-133225 | 6/2008 | |
| JP | 2008-214332 | 9/2008 | |
| JP | 2010-065033 | * 3/2010 | ............. H01L 51/50 |
| JP | 2010-65033 | 3/2010 | |
| JP | 2010-143841 | 7/2010 | |
| WO | WO 02/20459 A1 | 3/2002 | |
| WO | WO 2007/123137 A1 | 11/2007 | |
| WO | WO 2010/052852 A1 | 5/2010 | |
| WO | WO 2010/058995 A1 | 5/2010 | |

OTHER PUBLICATIONS

International Search Report and Written Opinion of the International Searching Authority issued Dec. 13, 2011, in PCT/JP2011/005930.
Korean Office Action issued Nov. 6, 2013, in Korea Patent Application No. 10-2011-7031467.

\* cited by examiner

*Primary Examiner* — Gregory Clark
(74) *Attorney, Agent, or Firm* — Oblon, McClelland, Maier & Neustadt, L.L.P.

(57) ABSTRACT

A compound is shown by the following formula (1).

$$\begin{array}{c}Ar^1\\ \diagdown\\ N-(Ar^5)_l-\overset{H}{C}=\overset{H}{C}-(Ar^6)_m-\left(\overset{H}{C}=\overset{}{\underset{H}{C}}-(Ar^7)_n\right)_p-N\overset{Ar^3}{\diagup}\\ \diagup\\ Ar^2\hspace{14em}Ar^4\end{array} \quad (1)$$

wherein l, m, and n are independently an integer from 1 to 3, $Ar^1$ to $Ar^4$ are independently a substituted or unsubstituted aryl group having 6 to 30 ring carbon atoms, or a substituted or unsubstituted heteroaryl group having 5 to 30 ring atoms, $Ar^5$, $Ar^6$, and $Ar^7$ are independently a substituted or unsubstituted arylene group having 6 to 30 ring carbon atoms, or a substituted or unsubstituted heteroarylene group having 5 to 30 ring atoms, and p is an integer from 0 to 2, and $Ar^6$ and N are bonded via a single bond when p is 0, provided that at least one of $Ar^1$ to $Ar^4$ is substituted with a substituted silyl group, a substituted or unsubstituted alkyl group having 1 to 20 carbon atoms, or a substituted or unsubstituted cycloalkyl group having 3 to 10 carbon atoms, and at least one of $Ar^1$ to $Ar^4$ is substituted with a cyano group.

25 Claims, No Drawings

AROMATIC AMINE DERIVATIVE AND ORGANIC ELECTROLUMINESCENCE DEVICE USING THE SAME

TECHNICAL FIELD

The invention relates to an aromatic amine derivative, and an organic electroluminescence device using the same.

BACKGROUND ART

An organic electroluminescence (EL) device that utilizes an organic substance is a promising inexpensive solid-state emitting large full-color display, and has been extensively developed. The organic EL device normally includes an emitting layer, and a pair of opposing electrodes disposed on either side of the emitting layer. When an electric field is applied between the electrodes, electrons and holes are injected into the emitting layer respectively from the cathode and the anode. The electrons and the holes recombine in the emitting layer to produce an excited state, and the energy is emitted as light when the excited state returns to the ground state.

In recent years, technology that increases the lifetime of the organic EL device has been developed, and applied to a full-color display (e.g., mobile phone or TV). However, a further improvement in emission properties (e.g., emission efficiency, lifetime, and color reproducibility) has been desired.

Patent Document 1 discloses a styryl compound that includes a specific end aryl group skeleton as a material for the organic EL device. This compound may improve the heat resistance, the luminous efficiency, the lifetime, and the blue purity of the organic EL device.

Patent Document 2 discloses a styryl compound in which the end aryl group is substituted with a specific substituent (silyl group) as a material for the organic EL device. This compound may improve the luminous efficiency and the lifetime of the organic EL device.

RELATED-ART DOCUMENT

Patent Document

Patent Document 1: WO2002/020459
Patent Document 2: WO2010/052852

SUMMARY OF THE INVENTION

An object of the invention is to provide a low-voltage (low power consumption) blue organic EL device, and an aromatic amine derivative for implementing such an organic EL device.

The invention provides the following aromatic amine derivative and the like.

1. A compound shown by a formula (1),

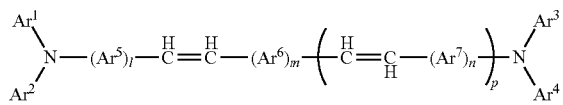

(1)

wherein l, m, and n are independently an integer from 1 to 3, $Ar^1$ to $Ar^4$ are independently a substituted or unsubstituted aryl group having 6 to 30 carbon atoms that form a ring (hereinafter referred to as "ring carbon atoms"), or a substituted or unsubstituted heteroaryl group having 5 to 30 atoms that form a ring (hereinafter referred to as "ring atoms"), $Ar^5$, $Ar^6$, and $Ar^7$ are independently a substituted or unsubstituted arylene group having 6 to 30 ring carbon atoms, or a substituted or unsubstituted heteroarylene group having 5 to 30 ring atoms, provided that when a plurality of $Ar^5$ are present, $Ar^5$s may be the same as or different from each other, when a plurality of $Ar^6$ are present, $Ar^6$s may be the same as or different from each other, and when a plurality of $Ar^7$ are present, $Ar^7$s may be the same as or different from each other, and p is an integer from 0 to 2, and $Ar^6$ and N are bonded via a single bond when p is 0, provided that at least one of $Ar^1$ to $Ar^4$ is substituted with a substituted silyl group, a substituted or unsubstituted alkyl group having 1 to 20 carbon atoms, or a substituted or unsubstituted cycloalkyl group having 3 to 10 carbon atoms, and at least one of $Ar^1$ to $Ar^4$ is substituted with a cyano group.

2. The compound according to 1, wherein two of $Ar^1$ to $Ar^4$ are substituted with a substituent, one of the two of $Ar^1$ to $Ar^4$ is substituted with a substituted silyl group, a substituted or unsubstituted alkyl group having 1 to 20 carbon atoms, or a substituted or unsubstituted cycloalkyl group having 3 to 10 carbon atoms, and the other of the two of $Ar^1$ to $Ar^4$ is substituted with a cyano group.

3. The compound according to 1 or 2, wherein two of $Ar^1$ to $Ar^4$ are independently substituted with a substituted silyl group, a substituted or unsubstituted alkyl group having 1 to 20 carbon atoms, or a substituted or unsubstituted cycloalkyl group having 3 to 10 carbon atoms, and the remainder of $Ar^1$ to $Ar^4$ are independently substituted with a cyano group.

4. The compound according to any one of 1 to 3, wherein $Ar^1$ to $Ar^4$ are independently a substituted or unsubstituted aryl group having 6 to 30 ring carbon atoms.

5. The compound according to any one of 1 to 4, wherein $Ar^1$ and $Ar^4$ are independently an aryl group having 6 to 30 ring carbon atoms that is substituted with a substituted silyl group, a substituted or unsubstituted alkyl group having 1 to 20 carbon atoms, or a substituted or unsubstituted cycloalkyl group having 3 to 10 carbon atoms, and $Ar^2$ and $Ar^3$ are independently an aryl group having 6 to 30 ring carbon atoms that is substituted with a cyano group.

6. The compound according to any one of 1 to 5, wherein $Ar^1$ and $Ar^4$ are independently a phenyl group that is substituted with a substituted silyl group, a substituted or unsubstituted alkyl group having 1 to 20 carbon atoms, or a substituted or unsubstituted cycloalkyl group having 3 to 10 carbon atoms, and $Ar^2$ and $Ar^3$ are independently a phenyl group that is substituted with a cyano group.

7. The compound according to any one of 1 to 6, wherein $Ar^5$, $Ar^6$, and $Ar^7$ are independently a substituted or unsubstituted arylene group having 6 to 30 ring carbon atoms.

8. The compound according to any one of 1 to 7, wherein $Ar^5$, $Ar^6$, and $Ar^7$ are independently a substituted or unsubstituted phenylene group, a substituted or unsubstituted naphthylene group, a substituted or unsubstituted biphenylene group, or a substituted or unsubstituted fluorenylene group.

9. The compound according to any one of 1 to 8, wherein l=1, m=1, and p=0.

10. The compound according to any one of 1 to 8, wherein l=1, m=1, n=1, and p=1.

11. The compound according to any one of 1 to 10, the compound being an emitting material for an organic electroluminescence device.

12. The compound according to any one of 1 to 10, the compound being a dopant material for an organic electroluminescence device.
13. An organic electroluminescence device including a cathode, an anode, and one or more organic thin film layers that comprise at least an emitting layer and are between the cathode and the anode, at least one organic thin film layer among the one or more organic thin film layers including the compound according to any one of 1 to 10 either alone or as a component of a mixture.
14. The organic electroluminescence device according to 13, wherein the at least one organic thin film layer that includes the compound according to any one of 1 to 10 is the emitting layer.
15. The organic electroluminescence device according to 13 or 14, wherein the at least one organic thin film layer that includes the compound according to any one of 1 to 10 further includes an anthracene derivative shown by a formula (5),

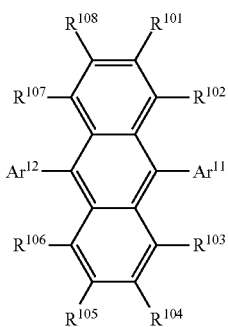

(5)

wherein $Ar^{11}$ and $Ar^{12}$ are independently a substituted or unsubstituted monocyclic group having 5 to 50 ring atoms, a substituted or unsubstituted fused cyclic group having 8 to 50 ring atoms, or a combination of the monocyclic group and the fused cyclic group, and $R^{101}$ to $R^{108}$ are independently a group selected from a hydrogen atom, a substituted or unsubstituted monocyclic group having 5 to 50 ring atoms, a substituted or unsubstituted fused cyclic group having 8 to 50 ring atoms, a combination of the monocyclic group and the fused cyclic group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

The invention thus provides a low-voltage (low power consumption) blue organic EL device, and an aromatic amine derivative for implementing such an organic EL device.

DESCRIPTION OF EMBODIMENTS

The aromatic amine derivative according to the invention is a compound shown by the following formula (1).

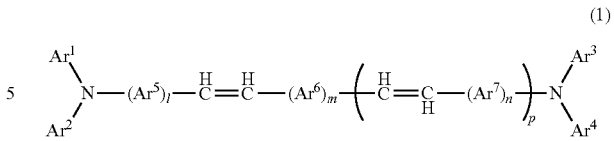

(1)

wherein l, m, and n are independently an integer from 1 to 3, $Ar^1$ to $Ar^4$ are independently a substituted or unsubstituted aryl group having 6 to 30 ring carbon atoms, or a substituted or unsubstituted heteroaryl group having 5 to 30 ring atoms, $Ar^5$, $Ar^6$, and $Ar^7$ are independently a substituted or unsubstituted arylene group having 6 to 30 ring carbon atoms, or a substituted or unsubstituted heteroarylene group having 5 to 30 ring atoms, provided that $Ar^5$s may be the same as or different from each other when l is an integer equal to or larger than 2, $Ar^6$s may be the same as or different from each other when m is an integer equal to or larger than 2, and $Ar^7$s may be the same as or different from each other when n is an integer equal to or larger than 2 (i.e., when a plurality of $Ar^5$ are present, $Ar^5$s may be the same as or different from each other, when a plurality of $Ar^6$ are present, $Ar^6$s may be the same as or different from each other, and when a plurality of $Ar^7$ are present, $Ar^7$s may be the same as or different from each other), and p is an integer from 0 to 2, and $Ar^6$ and N are bonded via a single bond when p is 0, provided that at least one of $Ar^1$ to $Ar^4$ is substituted with a substituted silyl group, a substituted or unsubstituted alkyl group having 1 to 20 carbon atoms, or a substituted or unsubstituted cycloalkyl group having 3 to 10 carbon atoms, and at least one of $Ar^1$ to $Ar^4$ is substituted with a cyano group.

In the aromatic amine derivative according to the invention, at least one of $Ar^1$ to $Ar^4$ is a group (substituted or unsubstituted aryl group having 6 to 30 ring carbon atoms, or substituted or unsubstituted heteroaryl group having 5 to 30 ring atoms) that is substituted with a substituted silyl group, a substituted or unsubstituted alkyl group having 1 to 20 carbon atoms, or a substituted or unsubstituted cycloalkyl group having 3 to 10 carbon atoms, and at least one of $Ar^1$ to $Ar^4$ is a group (substituted or unsubstituted aryl group having 6 to 30 ring carbon atoms, or substituted or unsubstituted heteroaryl group having 5 to 30 ring atoms) that is substituted with a cyano group.

Since the aromatic amine derivative according to the invention is substituted with a substituted silyl group, an alkyl group, or a cycloalkyl group, and is also substituted with a cyano group, the carrier injection capability is significantly improved when using the aromatic amine derivative as a dopant material for a host-dopant system. Therefore, an organic EL device that utilizes the aromatic amine derivative according to the invention implements a decrease in voltage, and also implements a reduction in power consumption due to a decrease in voltage.

It is preferable that $Ar^1$ to $Ar^4$ in the formula (1) are independently a substituted or unsubstituted aryl group having 6 to 30 ring carbon atoms.

Note that a substituted silyl group, an alkyl group, or a cycloalkyl group, and a cyano group may be bonded to an identical group among $Ar^1$ to $Ar^4$, or may be bonded to different groups among $Ar^1$ to $Ar^4$.

It is preferable that two of $Ar^1$ to $Ar^4$ be substituted with a substituent, one of the two of $Ar^1$ to $Ar^4$ be substituted with a substituted silyl group, a substituted or unsubstituted alkyl group having 1 to 20 carbon atoms, or a substituted or unsubstituted cycloalkyl group having 3 to 10 carbon atoms, and the other of the two of $Ar^1$ to $Ar^4$ be substituted with a cyano group.

It is also preferable that each of $Ar^1$ to $Ar^4$ be substituted with a substituent, two of $Ar^1$ to $Ar^4$ are groups (substituted or unsubstituted aryl group having 6 to 30 ring carbon atoms, or substituted or unsubstituted heteroaryl group having 5 to 30 ring atoms) that are substituted with a substituted silyl group, a substituted or unsubstituted alkyl group having 1 to 20 carbon atoms, or a substituted or unsubstituted cycloalkyl group having 3 to 10 carbon atoms, and the remainder of $Ar^1$ to $Ar^4$ are groups (substituted or unsubstituted aryl group having 6 to 30 ring carbon atoms, or substituted or unsubstituted heteroaryl group having 5 to 30 ring atoms) that are substituted with a cyano group.

It is also preferable that $Ar^1$ and $Ar^4$ are independently a substituted or unsubstituted aryl group having 6 to 30 ring carbon atoms that is substituted with a substituted silyl group, a substituted or unsubstituted alkyl group having 1 to 20 carbon atoms, or a substituted or unsubstituted cycloalkyl group having 3 to 10 carbon atoms, and $Ar^2$ and $Ar^3$ are independently a substituted or unsubstituted aryl group having 6 to 30 ring carbon atoms that is substituted with a cyano group. It is more preferable that $Ar^1$ and $Ar^4$ are independently a phenyl group that is substituted with a substituted silyl group, a substituted or unsubstituted alkyl group having 1 to 20 carbon atoms, or a substituted or unsubstituted cycloalkyl group having 3 to 10 carbon atoms, and $Ar^2$ and $Ar^3$ are independently a phenyl group that is substituted with a cyano group.

It is preferable that $Ar^5$, $Ar^6$, and $Ar^7$ in the formula (1) are independently a substituted or unsubstituted arylene group having 6 to 30 ring carbon atoms. It is more preferable that $Ar^5$, $Ar^6$, and $Ar^7$ are independently a substituted or unsubstituted phenylene group, a substituted or unsubstituted naphthylene group, a substituted or unsubstituted biphenylene group, or a substituted or unsubstituted fluorenylene group.

It is preferable that l=1, m=1, and p=0, or l=1, m=1, n=1, and p=1.

Each group included in the aromatic amine derivative according to the invention is described below.

Note that the term "ring carbon atom" used herein refers to a carbon atom that forms a saturated ring, an unsaturated ring, or an aromatic ring, and the term "ring atom" used herein refers to a carbon atom or a heteroatom that forms a heteroring (including a saturated ring, an unsaturated ring, and an aromatic ring).

The aryl group having 6 to 30 ring carbon atoms represented by $Ar^1$ to $Ar^4$ is preferably an aryl group having 6 to 20 ring carbon atoms, and more preferably an aryl group having 6 to 12 ring carbon atoms.

Specific examples of the aryl group include a phenyl group, a naphthyl group, an anthryl group, a phenanthryl group, a naphthacenyl group, a pyrenyl group, a chrysenyl group, a benzo[c]phenanthryl group, a benzo[g]chrysenyl group, a triphenylenyl group, a fluorenyl group, a 9,9-dimethylfluorenyl group, a benzofluorenyl group, a dibenzofluorenyl group, a biphenylyl group, a terphenyl group, a fluoranthenyl group, and the like. Among these, a phenyl group, a biphenyl group, a tolyl group, a xylyl group, and a naphthyl group are preferable.

The heteroaryl group having 5 to 30 ring atoms represented by $Ar^1$ to $Ar^4$ is preferably a heteroaryl group having 5 to 20 ring atoms, and more preferably a heteroaryl group having 5 to 14 ring atoms.

Specific examples of the heteroaryl group include a pyrrolyl group, a pyrazinyl group, a pyridinyl group, an indolyl group, an isoindolyl group, an imidazolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, a phenazinyl group, a phenothiazinyl group, a phenoxadinyl group, an oxazolyl group, an oxadiazolyl group, a furazanyl group, a thienyl group, a benzothiophenyl group, and the like. Among these, a dibenzofuranyl group, a dibenzothiophenyl group, and a carbazolyl group are preferable.

Examples of the substituted silyl group that may substitute at least one of $Ar^1$ to $Ar^4$ include substituted or unsubstituted alkylsilyl groups (including mono-, di-, and trialkylsilyl groups) having 1 to 20 carbon atoms, substituted or unsubstituted arylsilyl groups (including aryldialkylsilyl groups, diarylalkylsilyl groups, triarylsilyl groups) having 6 to 30 carbon atoms, and the like.

The alkylsilyl group having 1 to 20 carbon atoms is preferably an alkylsilyl group having 1 to 10 carbon atoms, and more preferably an alkylsilyl group having 1 to 6 carbon atoms. Specific examples of the alkylsilyl group include a trimethylsilyl group, a triethylsilyl group, a t-butyldimethylsilyl group, a vinyldimethylsilyl group, a propyldimethylsilyl group, and the like.

The arylsilyl group having 6 to 30 carbon atoms is preferably an arylsilyl group having 6 to 20 carbon atoms, and more preferably an arylsilyl group having 6 to 10 carbon atoms. Specific examples of the arylsilyl group include a triphenylsilyl group, a phenyldimethylsilyl group, a t-butyldiphenylsilyl group, a tritolylsilyl group, a trixylylsilyl group, a trinaphthylsilyl group, and the like.

Examples of the substituted or unsubstituted alkyl group having 1 to 20 carbon atoms that may substitute at least one of $Ar^1$ to $Ar^4$ include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, and the like.

The number of carbon atoms is preferably 1 to 10, and more preferably 1 to 6. A methyl group, an ethyl group, a propyl group, an isopropyl group, an n-butyl group, an s-butyl group, an isobutyl group, a t-butyl group, an n-pentyl group, and an n-hexyl group are preferable as the substituted or unsubstituted alkyl group having 1 to 20 carbon atoms.

A substituent that may substitute the alkyl group having 1 to 20 carbon atoms is preferably an aryl group having 6 to 12 ring carbon atoms, and more preferably a phenyl group.

The substituted alkyl group having 1 to 20 carbon atoms is preferably a phenylmethyl group, a phenylethyl group, a phenylpropyl group (e.g., 2-phenylisopropyl group), or the like.

Examples of the substituted or unsubstituted cycloalkyl group having 3 to 10 carbon atoms that may substitute at least one of $Ar^1$ to $Ar^4$ include a cyclopropyl group, a cyclobutyl group, a cyclopentyl group, a cyclohexyl group, a 4-methylcyclohexyl group, an adamantyl group, a norbornyl group, and the like. The number of ring carbon atoms is preferably 3 to 10, more preferably 3 to 8, and particularly preferably 3 to 6.

Specific examples of the arylene group having 6 to 30 (preferably 6 to 20, and more preferably 6 to 12) ring carbon atoms and the heteroarylene group having 5 to 30 (preferably 5 to 20, and more preferably 5 to 14) ring atoms represented by $Ar^5$, $Ar^6$, and $Ar^7$ include divalent groups that correspond to the aryl group having 6 to 30 ring carbon atoms and the heteroaryl group having 5 to 30 ring atoms represented by $Ar^1$ to $Ar^4$. The arylene group and the heteroarylene group are preferably divalent groups that correspond to a phenyl group, a fluorenyl group, a 9,9-dimethylfluorenyl group, a naphthyl group, a phenanthryl group, a biphenylyl group, a dibenzofluorenyl group, a pyridinyl group, an isoquinolyl group, and the like.

Examples of a substituent that may substitute each substituted or unsubstituted group in the formula (1) include an alkyl group, a substituted silyl group, an aryl group, a cycloalkyl group, a heteroaryl group (as described above), an alkoxy group, an aryloxy group, an aralkyl group, a halogen atom, an alkyl halide group (as described below), a silyl group, a hydroxyl group, a nitro group, a cyano group, a carboxyl group, and the like.

The term "unsubstituted" used herein refers to substitution with a hydrogen atom. The term "hydrogen atom" used herein includes light hydrogen, deuterium, and tritium.

When $Ar^1$ to $Ar^4$ are independently a group (aryl group having 6 to 30 ring carbon atoms, or heteroaryl group having 5 to 30 ring atoms) substituted with a substituent, a compound in which a substituted silyl group, a substituted or unsubstituted alkyl group having 1 to 20 carbon atoms, a substituted or unsubstituted cycloalkyl group having 3 to 10 carbon atoms, or a cyano group is bonded to the substituent also falls under the compound according to the invention. For example, when $Ar^1$ to $Ar^4$ are substituted with an aryl group having 6 to 30 ring carbon atoms, a substituted silyl group, a substituted or unsubstituted alkyl group having 1 to 20 carbon atoms, a substituted or unsubstituted cycloalkyl group having 3 to 10 carbon atoms, or a cyano group may be bonded to the aryl group (substituent).

An alkoxy group is shown by -OY. Examples of Y include the above alkyl groups. Examples of the alkoxy group include a methoxy group and an ethoxy group.

An aryloxy group is shown by -OZ. Examples of Z include the above aryl groups. Examples of the aryloxy group include a phenoxy group.

An aralkyl group is shown by -Y-Z. Examples of Y include alkylene groups that correspond to the above alkyl groups. Examples of Z include the above aryl groups. The number of carbon atoms of the aralkyl group is 7 to 50 (the number of carbon atoms of the aryl moiety is 6 to 49 (preferably 6 to 30, more preferably 6 to 20, and particularly preferably 6 to 12), and the number of carbon atoms of the alkyl moiety is 1 to 44 (preferably 1 to 30, more preferably 1 to 20, still more preferably 1 to 10, and particularly preferably 1 to 6). Examples of the aralkyl group include a benzyl group, a phenylethyl group, and a 2-phenylpropan-2-yl group.

Examples of the halogen atom include a fluorine atom, a chlorine atom, a bromine atom, an iodine atom, and the like. Among these, a fluorine atom is preferable.

Examples of the alkyl halide group include a fluoromethyl group, a difluoromethyl group, a trifluoromethyl group, a fluoroethyl group, a trifluoromethylmethyl group, and the like.

Specific examples of the aromatic amine derivative according to the invention are shown below.

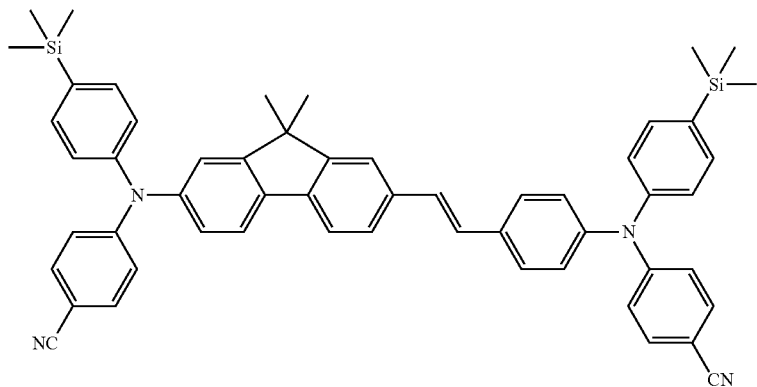

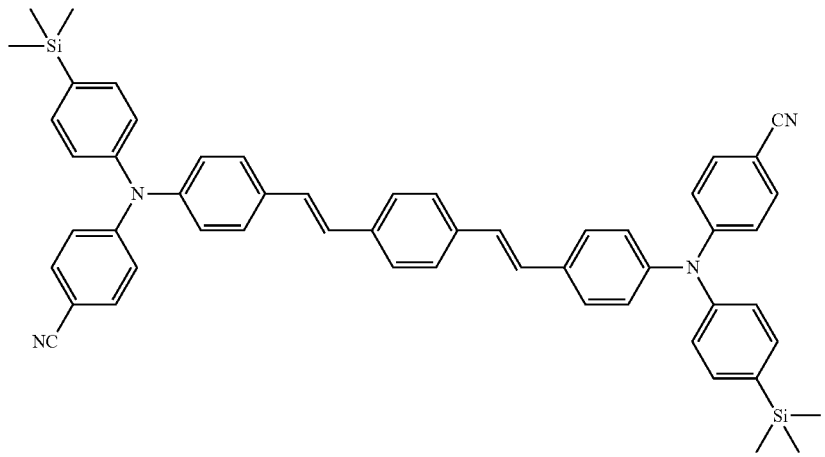

-continued
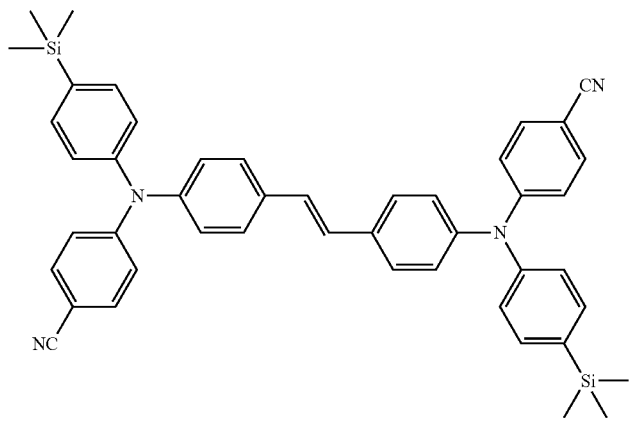
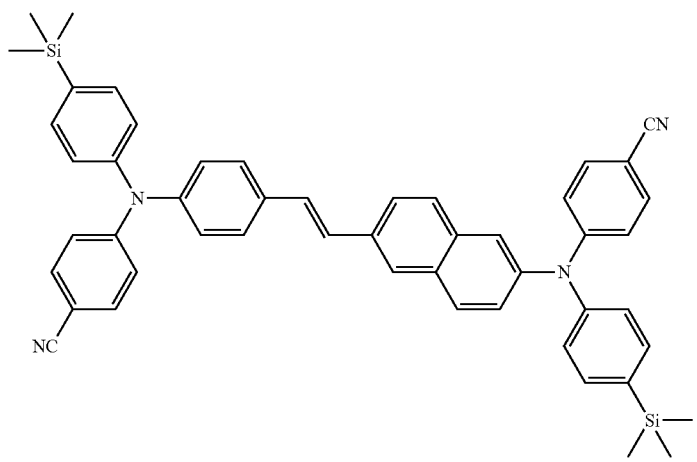
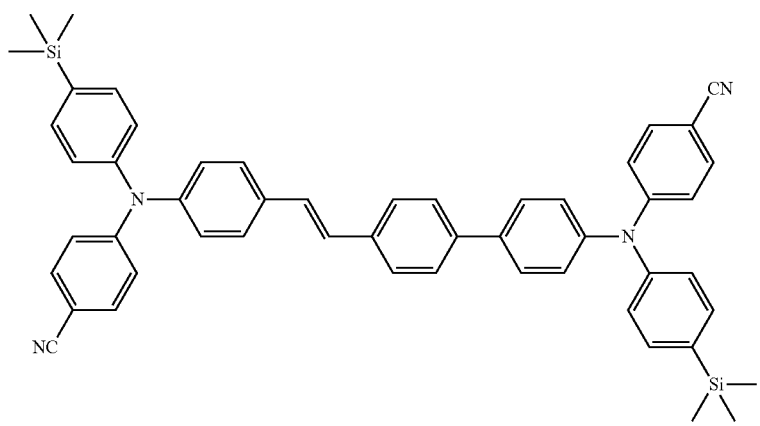
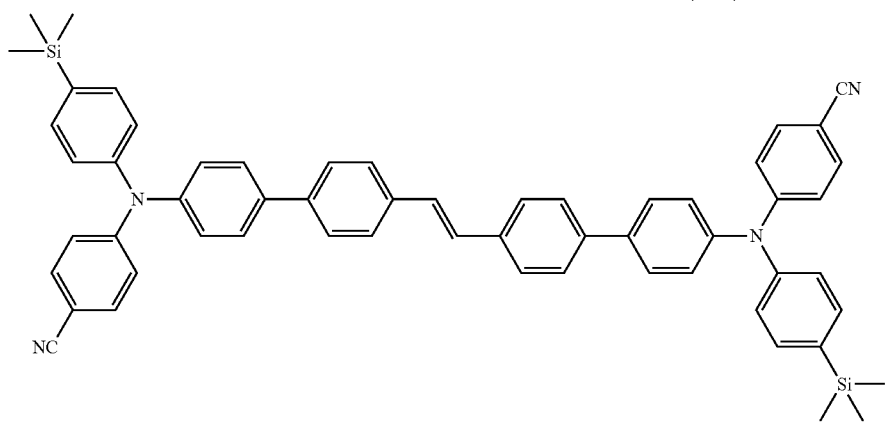

-continued
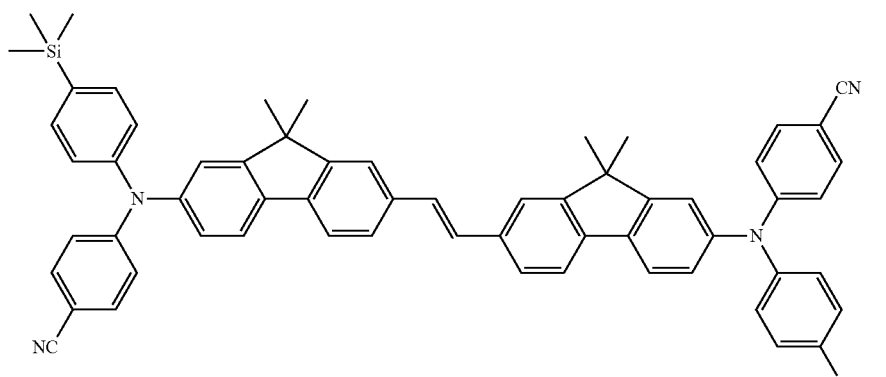
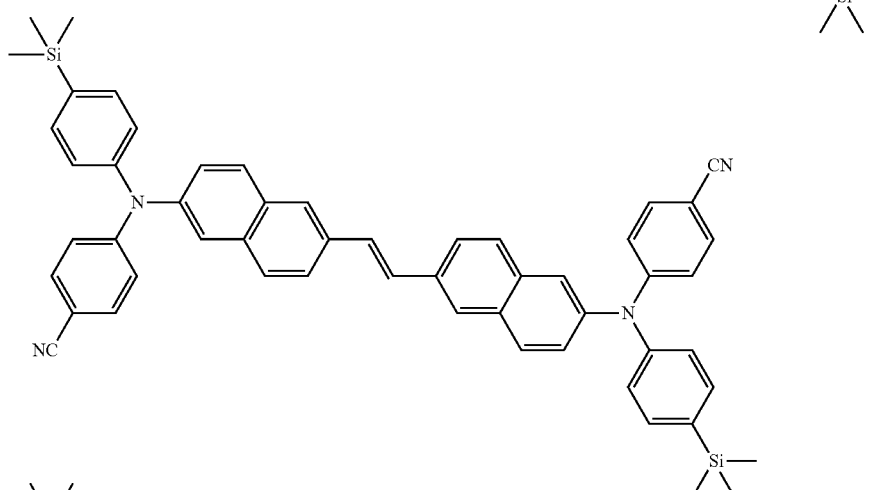
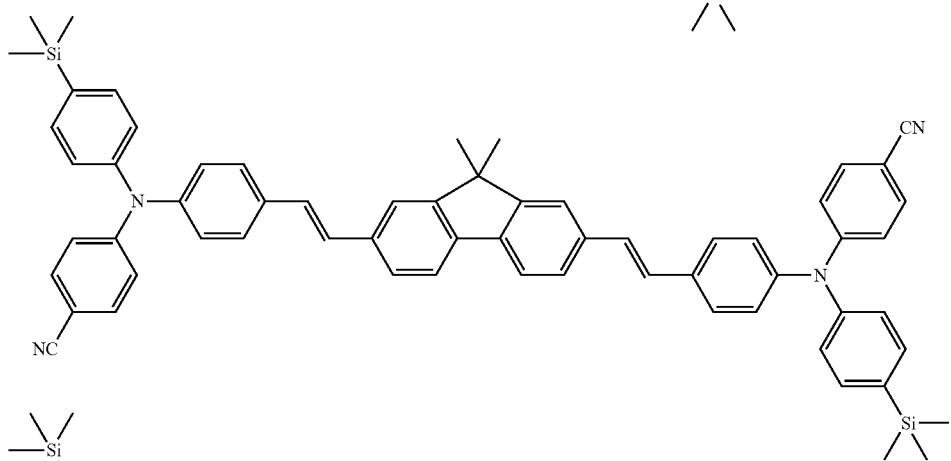
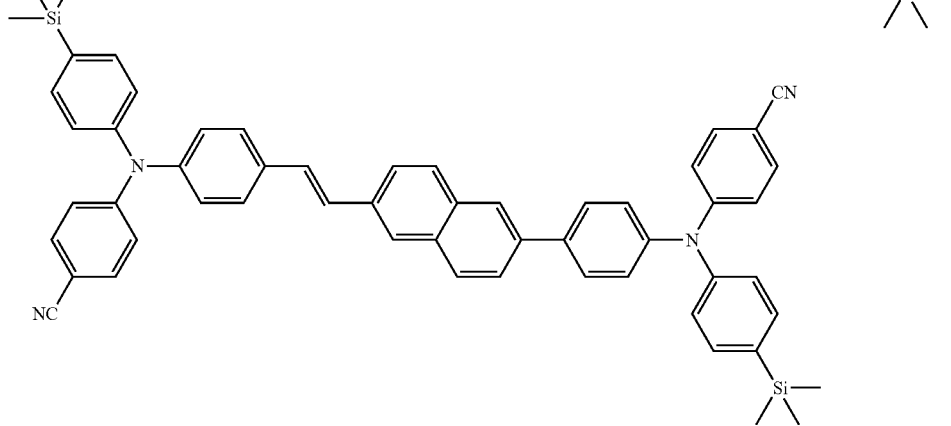

-continued
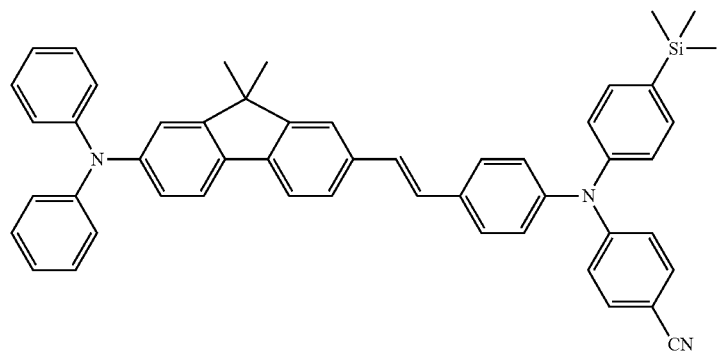
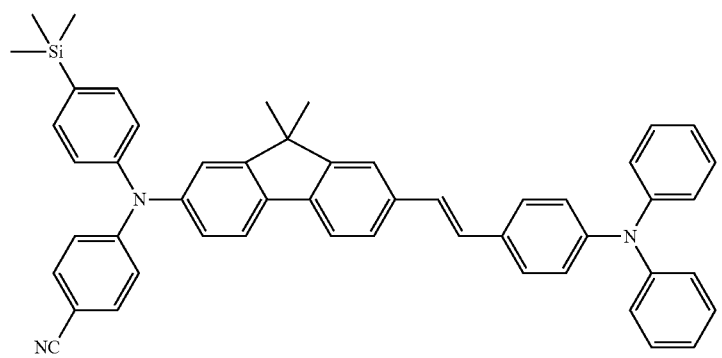
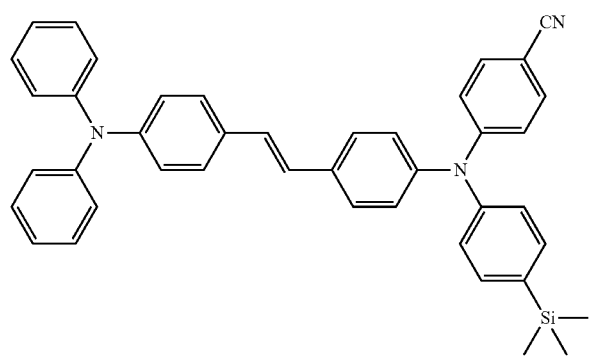
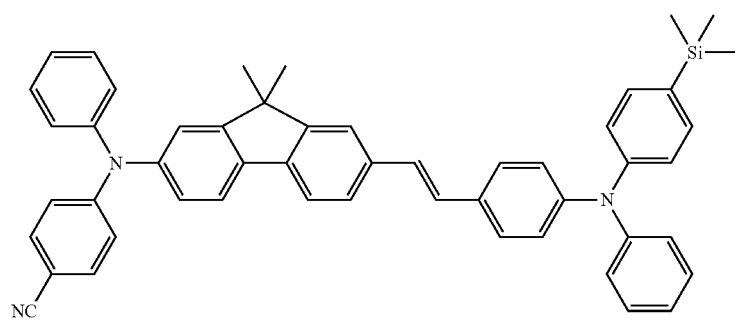

-continued
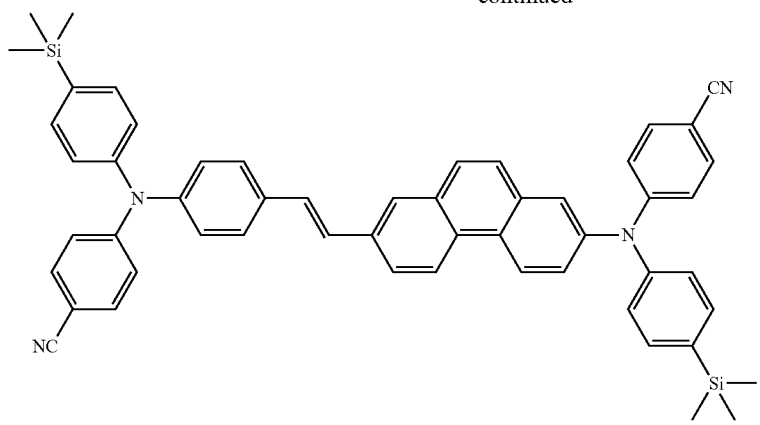
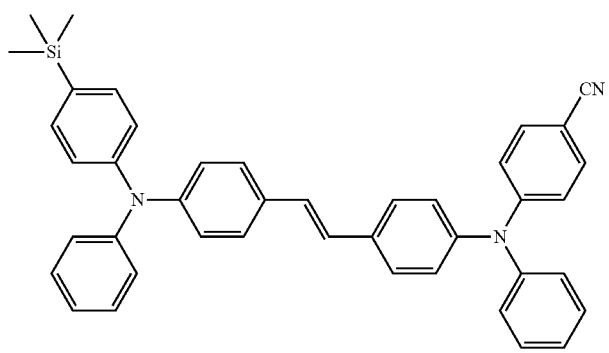
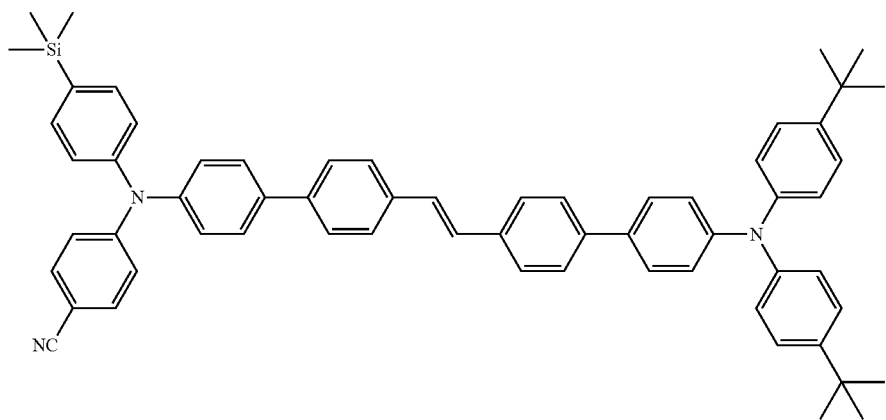
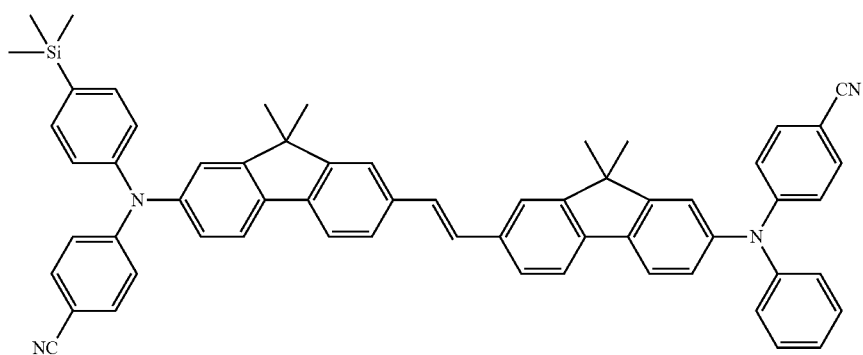

-continued
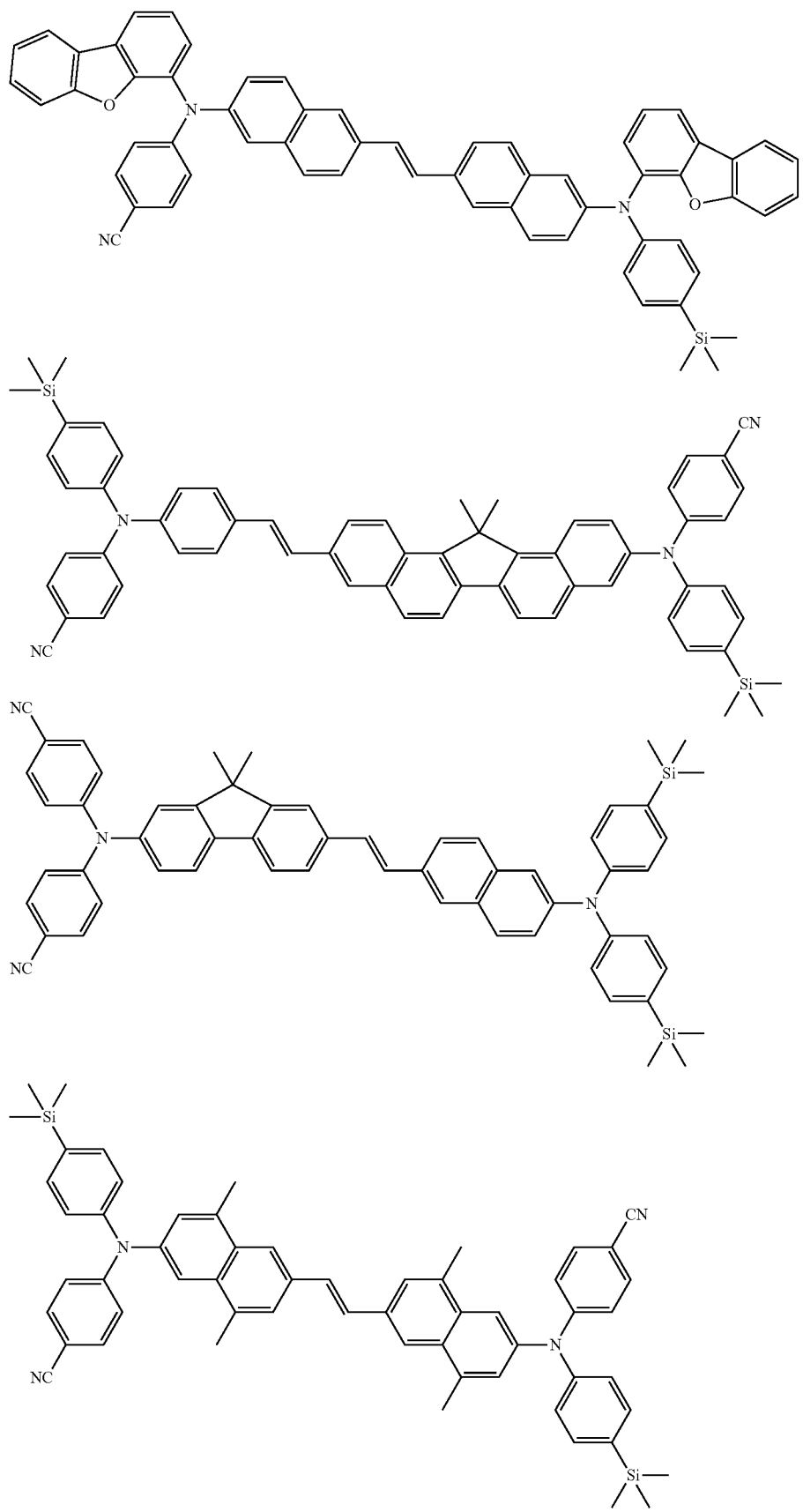

-continued
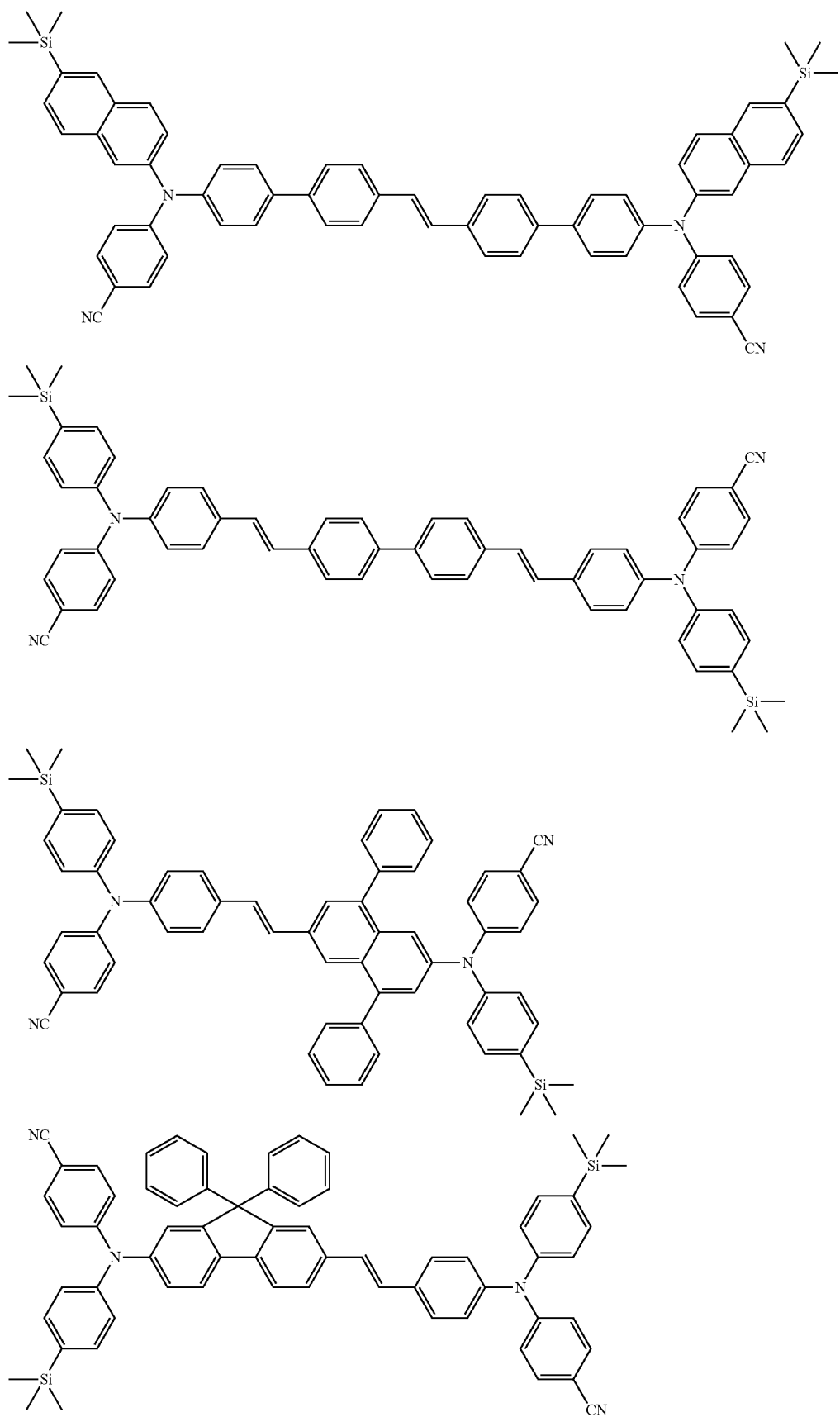

-continued
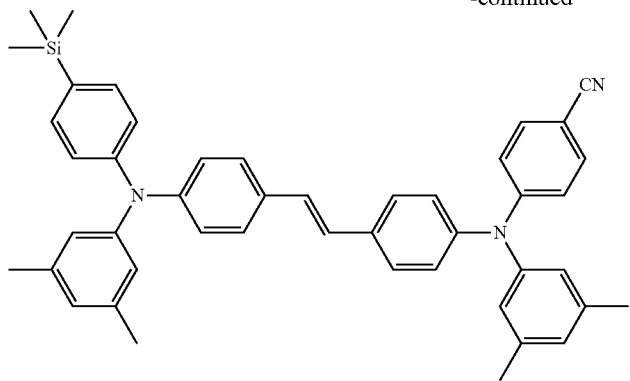
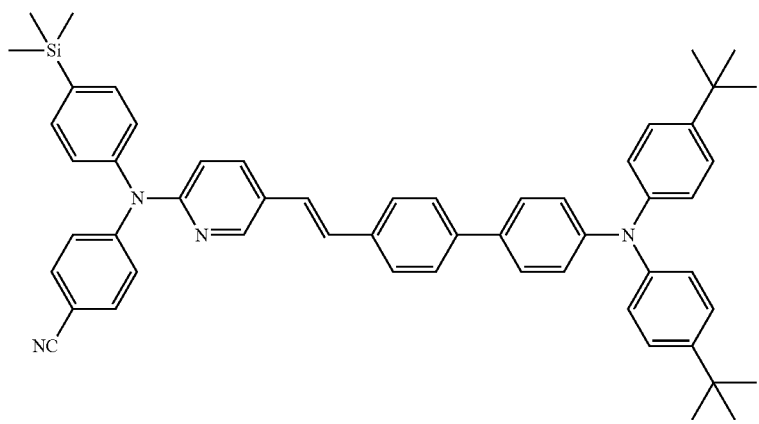
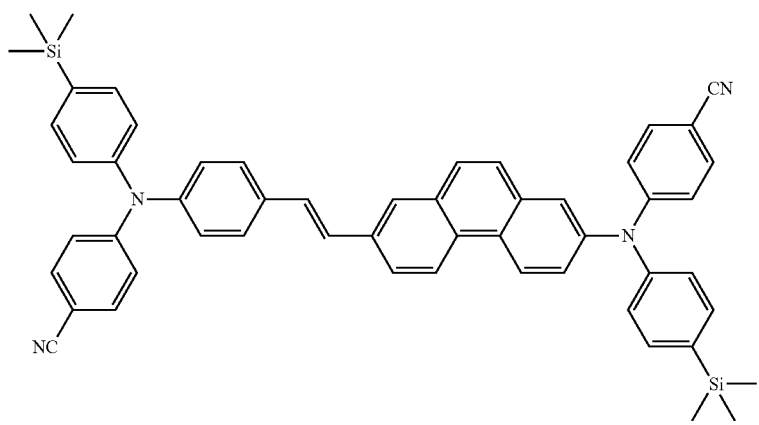
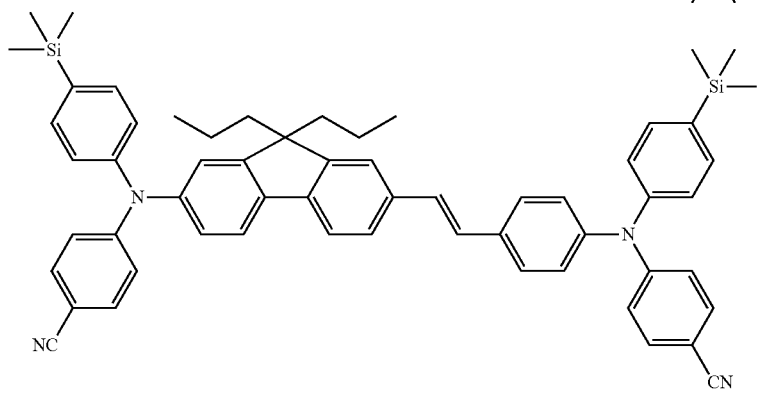

-continued
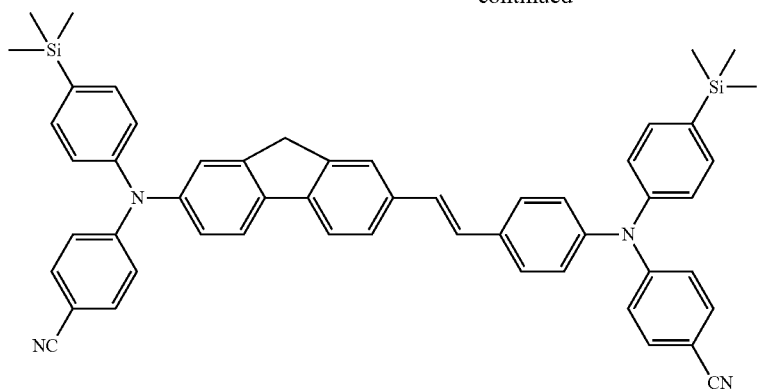
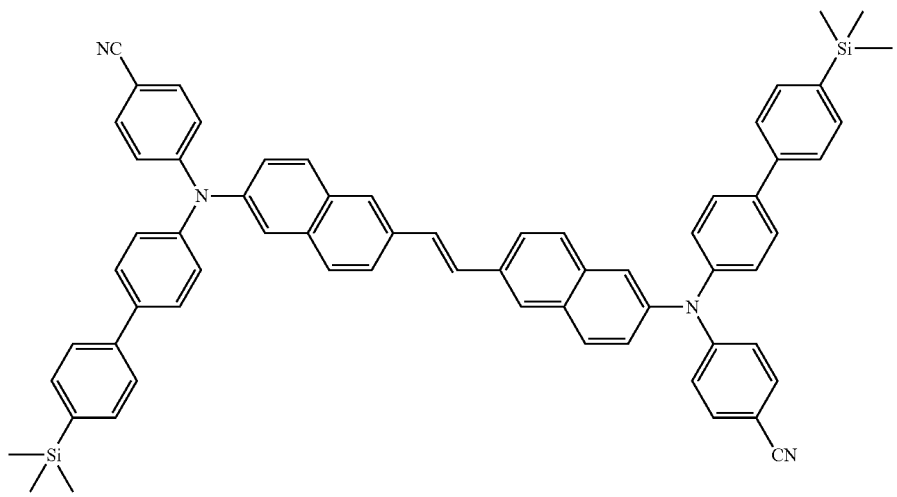
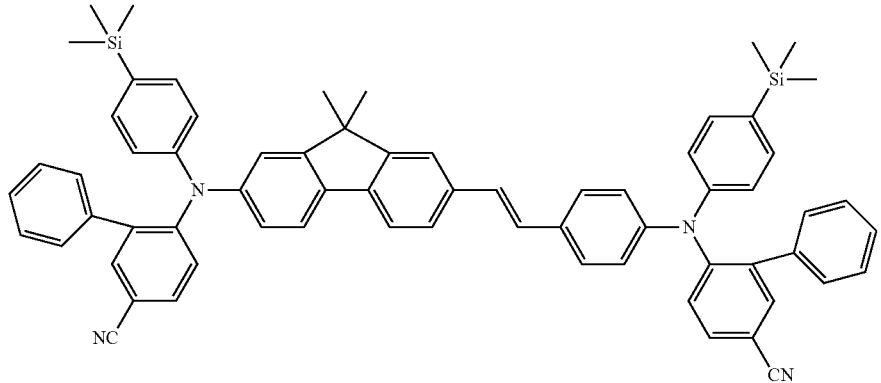
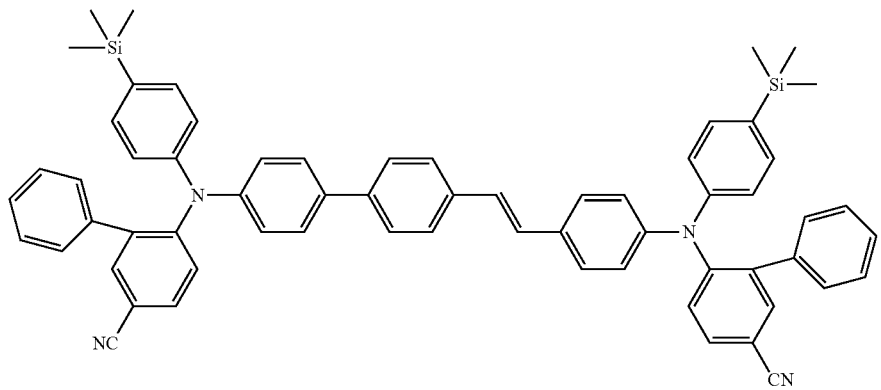

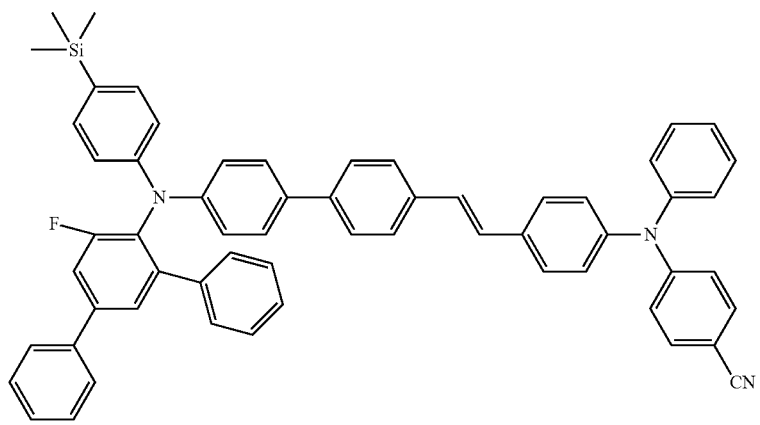

-continued
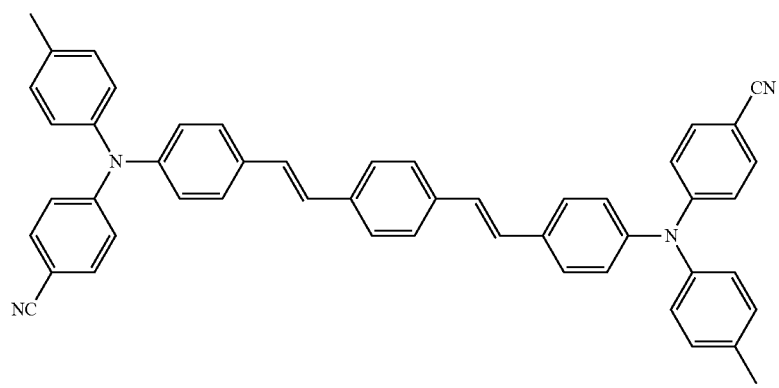
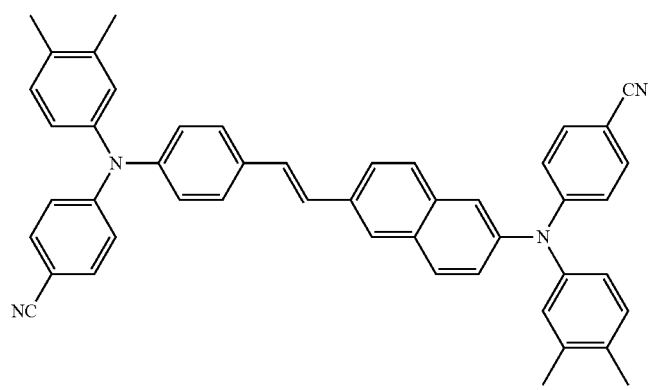
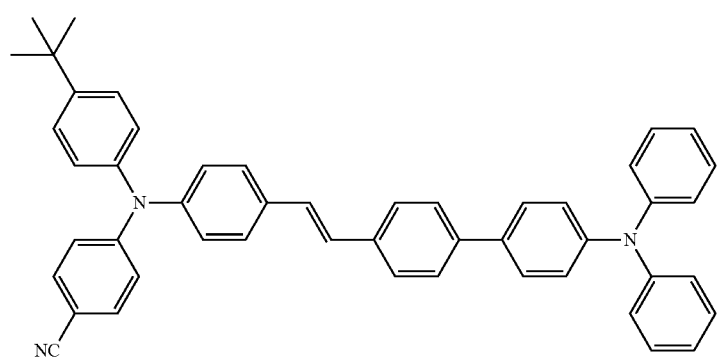
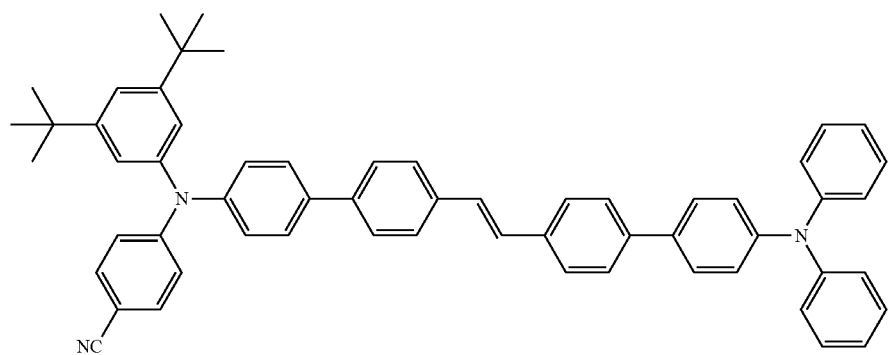

-continued
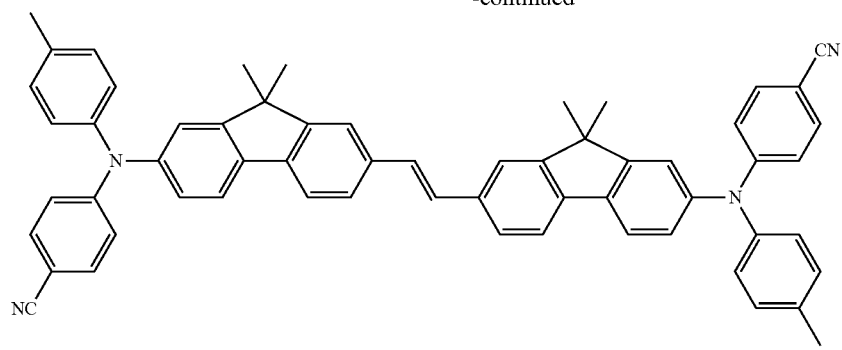
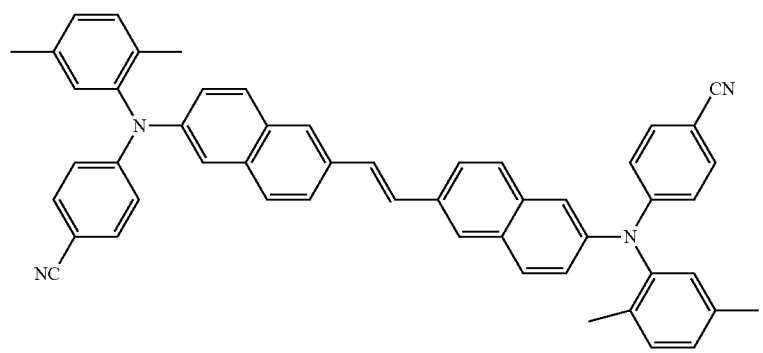
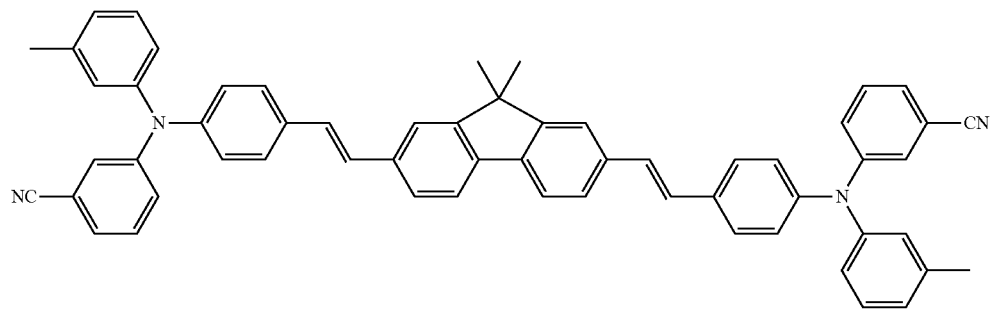
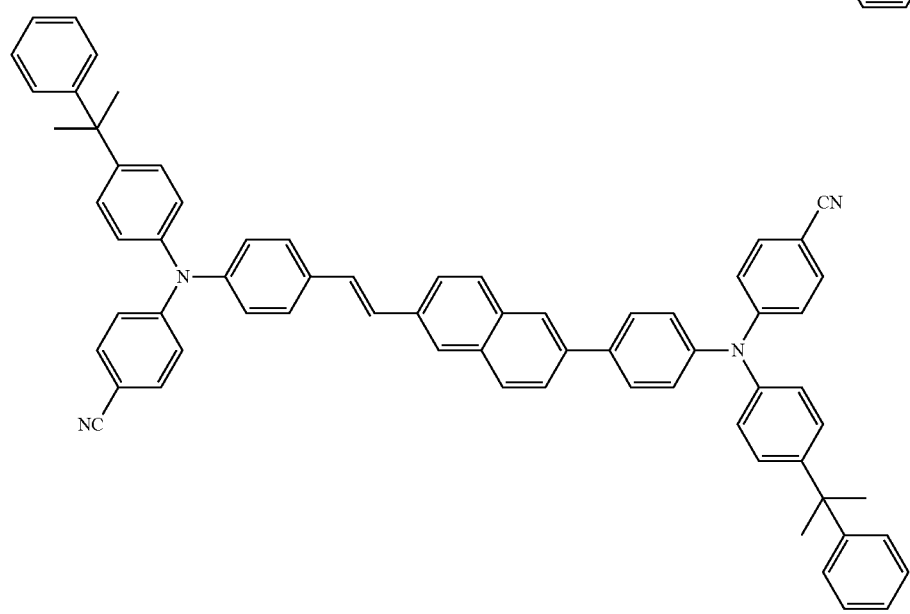

-continued
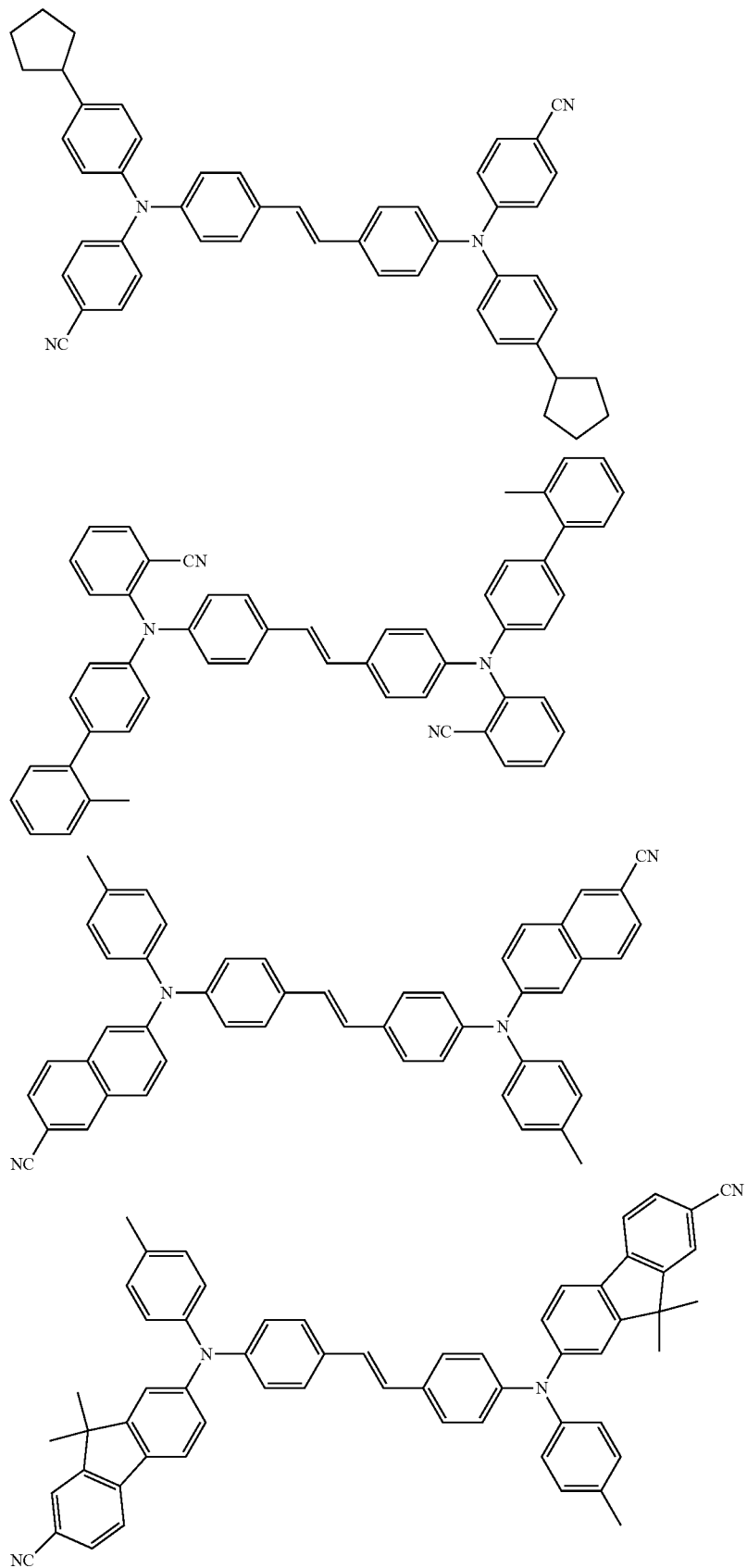

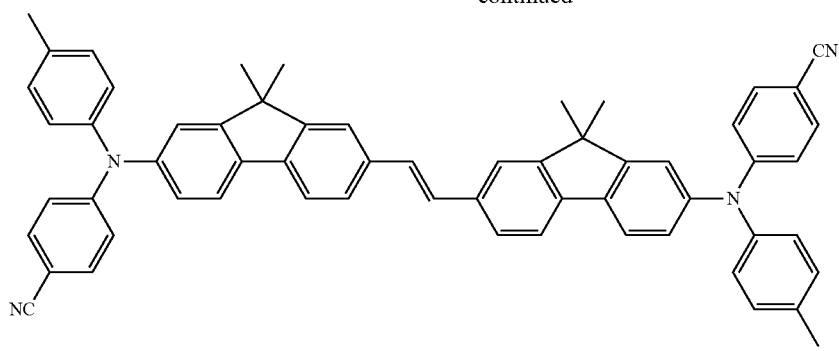
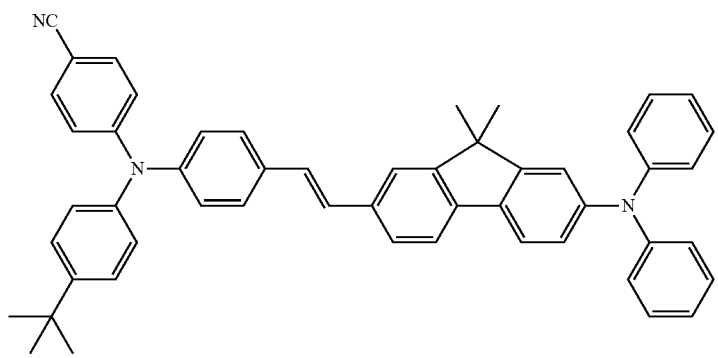
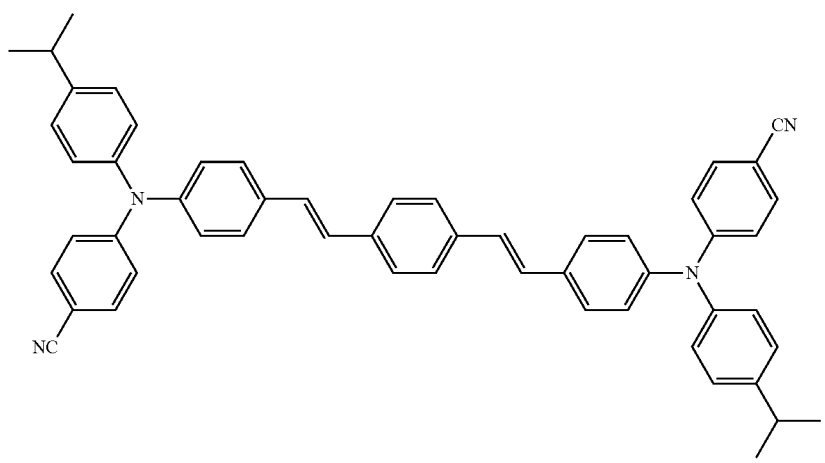
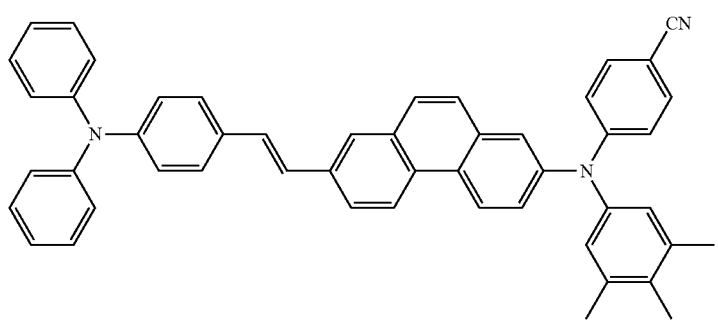

-continued
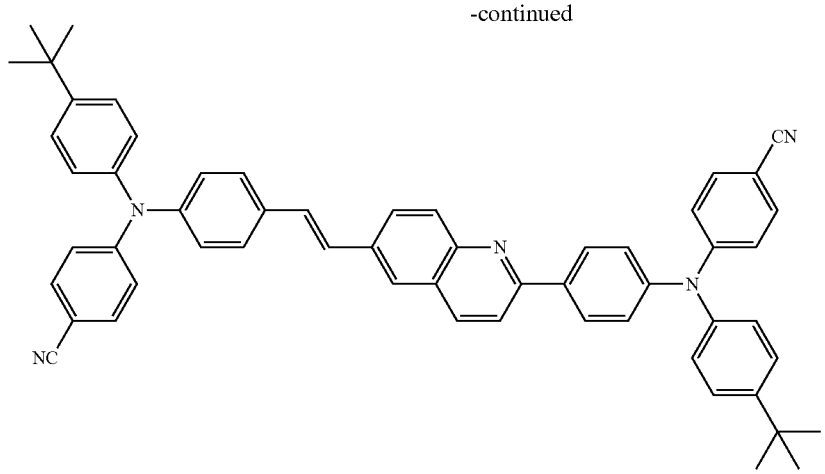
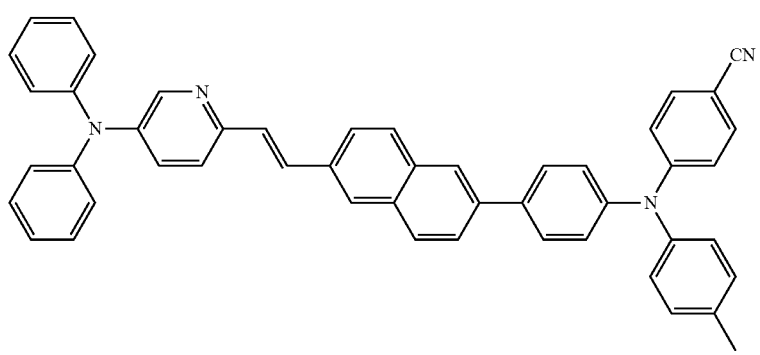
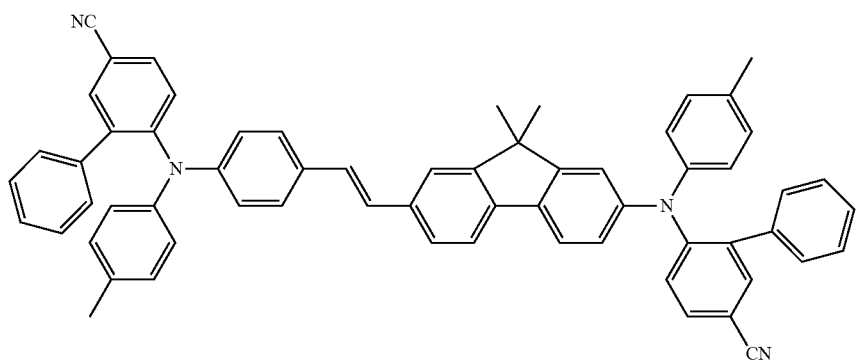
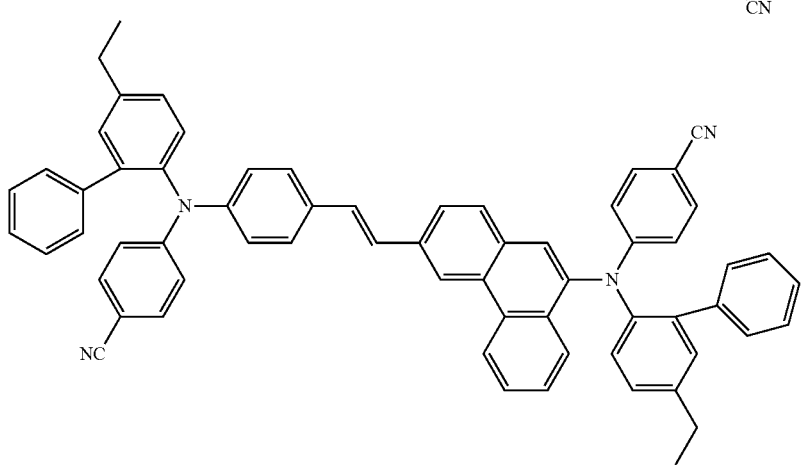

-continued

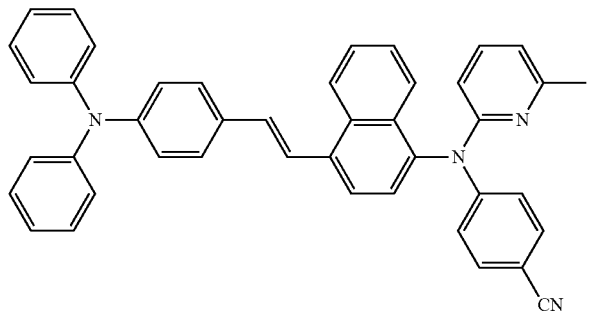

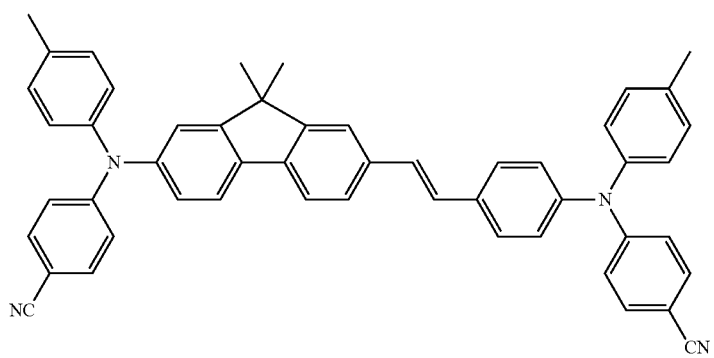

The aromatic amine derivative according to the invention may suitably be used as an emitting material (e.g., dopant) used for an organic electroluminescence device.

The organic electroluminescence device according to the invention includes a cathode, an anode, and one or more organic thin film layers that include at least an emitting layer and are between the cathode and the anode, at least one organic thin film layer among the one or more organic thin film layers including the aromatic amine derivative according to the invention either alone or as a component of a mixture.

The organic thin film layer that includes the aromatic amine derivative according to the invention is preferably the emitting layer. The emitting layer may include only the aromatic amine derivative according to the invention, or may include the aromatic amine derivative according to the invention as a host or a dopant.

In the organic electroluminescence device according to the invention, it is preferable that at least one organic thin film layer among the one or more organic thin film layers include the aromatic amine derivative, and at least one of an anthracene derivative shown by the following formula (5) and a pyrene derivative shown by the following formula (6). It is preferable that the emitting layer include the aromatic amine derivative as a dopant, and include the anthracene derivative as a host.

(Anthracene Derivative)

The anthracene derivative is shown by the following formula (5).

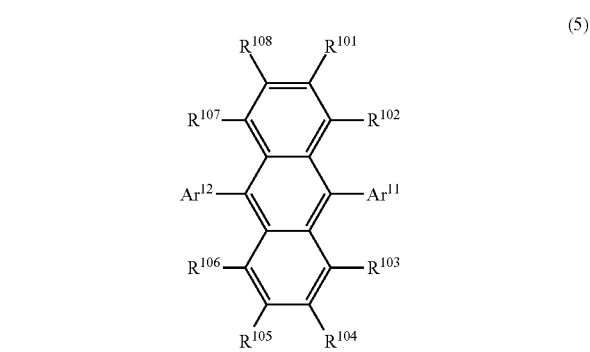

(5)

wherein $Ar^{11}$ and $Ar^{12}$ are independently a substituted or unsubstituted monocyclic group having 5 to 50 ring atoms, a substituted or unsubstituted fused cyclic group having 8 to 50 ring atoms, or a combination of the monocyclic group and the fused cyclic group, and $R^{101}$ to $R^{108}$ are independently a group selected from a hydrogen atom, a substituted or unsubstituted monocyclic group having 5 to 50 ring atoms, a substituted or unsubstituted fused cyclic group having 8 to 50 ring atoms, a combination of the monocyclic group and the fused cyclic group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

The term "monocyclic group" used herein refers to a group that includes only a cyclic structure that does not have a fused structure.

Specific examples of a preferable monocyclic group having 5 to 50 (preferably 5 to 30, and more preferably 5 to 20) ring atoms include aromatic groups (e.g., phenyl group, biphenyl group, terphenyl group, and quarter phenyl group) and heterocyclic groups (e.g., pyridyl group, pyrazyl group, pyrimidyl group, triazinyl group, furyl group, and thienyl group).

Among these, a phenyl group, a biphenyl group, and a terphenyl group are preferable.

The term "fused cyclic group" used herein refers to a group in which two or more cyclic structures are fused.

Specific examples of a preferable fused cyclic group having 8 to 50 (preferably 8 to 30, and more preferably 8 to 20) ring atoms include fused aromatic ring groups (e.g., naphthyl group, phenanthryl group, anthryl group, chrysenyl group, benzanthryl group, benzophenanthryl group, triphenylenyl group, benzochrysenyl group, indenyl group, fluorenyl group, 9,9-dimethylfluorenyl group, benzofluorenyl group, dibenzofluorenyl group, fluoranthenyl group, and benzofluoranthenyl group) and fused heterocyclic groups (e.g., benzofuranyl group, benzothiophenyl group, indolyl group, dibenzofuranyl group, dibenzothiophenyl group, carbazolyl group, quinolyl group, and phenanthrolinyl group).

Among these, a naphthyl group, a phenanthryl group, an anthryl group, a 9,9-dimethylfluorenyl group, a fluoranthenyl group, a benzanthryl group, a dibenzothiophenyl group, a dibenzofuranyl group, and a carbazolyl group are preferable.

Examples of the alkyl group, the substituted silyl group, the alkoxy group, the aryloxy group, the aralkyl group, the cycloalkyl group, and the halogen atom in the formula (5) include those mentioned above in connection with each group and substituent in the formula (1). Only preferable specific examples of each group in the formula (5) are given below.

A substituent that may substitute $Ar^{11}$, $Ar^{12}$, and $R^{101}$ to $R^{108}$ is preferably a monocyclic group, a fused cyclic group, an alkyl group, a cycloalkyl group, a substituted or unsubstituted silyl group, an alkoxy group, a cyano group, or a halogen atom (particularly a fluorine atom), and particularly preferably a monocyclic group or a fused cyclic group. Specific examples of a preferable substituent include those mentioned above in connection with each group in the formulas (1) and (5).

The anthracene derivative shown by the formula (5) is preferably any of the following anthracene derivatives (A), (B), and (C). The anthracene derivative is selected depending on the configuration and the desired properties of the organic EL device.

(Anthracene Derivative (A))

The anthracene derivative (A) is an anthracene derivative shown by the formula (5) wherein $Ar^{11}$ and $Ar^{12}$ are independently a substituted or unsubstituted fused cyclic group having 8 to 50 ring atoms. The anthracene derivative (A) may be an anthracene derivative wherein $Ar^{11}$ and $Ar^{12}$ are identical substituted or unsubstituted fused cyclic groups, or may be an anthracene derivative wherein $Ar^{11}$ and $Ar^{12}$ are different substituted or unsubstituted fused cyclic groups.

The anthracene derivative (A) is particularly preferably an anthracene derivative wherein $Ar^{11}$ and $Ar^{12}$ are different substituted or unsubstituted fused cyclic groups (including a difference in position of a substituent). Specific examples of a preferable fused cyclic group include those mentioned above. A naphthyl group, a phenanthryl group, a benzanthryl group, a 9,9-dimethylfluorenyl group, and a dibenzofuranyl group are preferable as the fused cyclic group.

(Anthracene Derivative (B))

The anthracene derivative (B) is an anthracene derivative shown by the formula (5) wherein one of $Ar^{11}$ and $Ar^{12}$ is a substituted or unsubstituted monocyclic group having 5 to 50 ring atoms, and the other of $Ar^{11}$ and $Ar^{12}$ is a substituted or unsubstituted fused cyclic group having 8 to 50 ring atoms.

It is preferable that $Ar^{12}$ be a naphthyl group, a phenanthryl group, a benzanthryl group, a 9,9-dimethylfluorenyl group, or a dibenzofuranyl group, and $Ar^{11}$ be a phenyl group substituted with a monocyclic group or a fused cyclic group.

Specific examples of a preferable monocyclic group and a preferable fused cyclic group include those mentioned above.

It is also preferable that $Ar^{12}$ be a fused cyclic group, and $Ar^{11}$ be an unsubstituted phenyl group. In this case, a phenanthryl group, a 9,9-dimethylfluorenyl group, a dibenzofuranyl group, and a benzanthryl group are particularly preferable as the fused cyclic group.

(Anthracene Derivative (C))

The anthracene derivative (C) is an anthracene derivative shown by the formula (5) wherein $Ar^{11}$ and $Ar^{12}$ are independently a substituted or unsubstituted monocyclic group having 5 to 50 ring atoms.

It is preferable that $Ar^{11}$ and $Ar^{12}$ be substituted or unsubstituted phenyl groups.

It is more preferable that $Ar^{11}$ be an unsubstituted phenyl group, and $Ar^{12}$ be a phenyl group substituted with a monocyclic group or a fused cyclic group, or $Ar^{11}$ and $Ar^{12}$ be independently a phenyl group substituted with a monocyclic group or a fused cyclic group.

Specific examples of a preferable monocyclic group and a preferable fused cyclic group as a substituent include those mentioned above. The monocyclic group as a substituent is preferably a phenyl group or a biphenyl group, and the fused cyclic group as a substituent is preferably a naphthyl group, a phenanthryl group, a 9,9-dimethylfluorenyl group, a dibenzofuranyl group, or a benzanthryl group.

In the organic electroluminescence device according to the invention, at least one organic thin film layer among the one or more organic thin film layers may include the aromatic amine derivative shown by the formula (1) and a pyrene derivative shown by the following formula (6). It is preferable that the emitting layer include the aromatic amine derivative as a dopant, and include the pyrene derivative as a host.

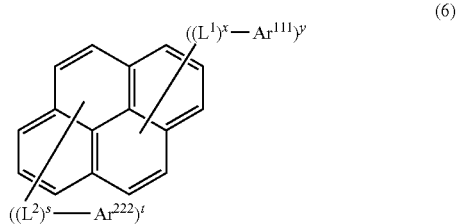

(6)

wherein $Ar^{111}$ and $Ar^{222}$ are independently a substituted or unsubstituted aryl group having 6 to 30 ring carbon atoms, $L^1$ and $L^2$ are independently a substituted or unsubstituted divalent aryl group having 6 to 30 ring carbon atoms, or a heterocyclic group, x is an integer from 0 to 1, y is an integer from 1 to 4, s is an integer from 0 to 1, and t is an integer from 0 to 3.

$L^1$ or $Ar^{111}$ is bonded to one of positions 1 to 5 of pyrene, and $L^2$ or $Ar^{222}$ is bonded to one of positions 6 to 10 of pyrene.

$L^1$ and $L^2$ in the formula (6) are preferably a substituted or unsubstituted phenylene group, a substituted or unsubstituted biphenylene group, a substituted or unsubstituted naphthylene group, a substituted or unsubstituted terphenylene group, a substituted or unsubstituted fluorenylene group, and a divalent aryl group including a combination thereof.

Examples of a substituent include those mentioned above in connection with the formula (1). A substituent that may substitute $L^1$ and $L^2$ is preferably an alkyl group having 1 to 20 carbon atoms.

x in the formula (6) is preferably an integer from 0 to 1. y in the formula (6) is preferably an integer from 1 to 2. s in the formula (6) is preferably an integer from 0 to 1.

t in the formula (6) is preferably an integer from 0 to 2.

Examples of the aryl group represented by $Ar^{111}$ and $Ar^{222}$ include those mentioned above in connection with the formula (1). $Ar^{111}$ and $Ar^{222}$ are preferably substituted or unsubstituted aryl groups having 6 to 20 ring carbon atoms, and more preferably substituted or unsubstituted aryl groups having 6 to 16 ring carbon atoms. Specific examples of a preferable aryl group include a phenyl group, a naphthyl group, a phenanthryl group, a fluorenyl group, a biphenyl group, an anthryl group, and a pyrenyl group.

When the emitting layer includes the aromatic amine derivative as a dopant, the content of the aromatic amine derivative in the emitting layer is preferably 0.1 to 20 mass %, and more preferably 1 to 10 mass %.

The aromatic amine derivative may be used for a hole-injecting layer, a hole-transporting layer, an electron-injecting layer, or an electron-transporting layer in addition to the emitting layer.

When the organic EL device includes a plurality of organic thin film layers, the organic EL device may have an (anode/hole-injecting layer/emitting layer/cathode) stacked structure, an (anode/emitting layer/electron-injecting layer/cathode) stacked structure, an (anode/hole-injecting layer/emitting layer/electron-injecting layer/cathode) stacked structure, an (anode/hole-injecting layer/hole-transporting layer/emitting layer/electron-injecting layer/cathode) stacked structure, or the like.

When the organic EL device includes a plurality of organic thin film layers, a decrease in luminance or lifetime due to quenching can be prevented. An emitting material, a dopant material, a hole-injecting material, and an electron-injecting material may optionally be used in combination. The luminance or the luminous efficiency may be improved due to the dopant material. The hole-injecting layer, the emitting layer, and the electron-injecting layer may respectively include two or more layers. When the hole-injecting layer includes two or more layers, a layer into which holes are injected from the electrode is referred to as "hole-injecting layer", and a layer that receives holes from the hole-injecting layer and transports the holes to the emitting layer is referred to as "hole-transporting layer". When the electron-injecting layer includes two or more layers, a layer into which electrons are injected from the electrode is referred to as "electron-injecting layer", and a layer that receives electrons from the electron-injecting layer and transports the electrons to the emitting layer is referred to as "electron-transporting layer". Each layer is selected depending on the energy level, the heat resistance, adhesion to an organic layer or a metal electrode, and the like of the material.

Examples of a material other than the anthracene derivative shown by the formula (5) that may be used for the emitting layer together with the aromatic amine derivative according to the invention include, but are not limited to, fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, and spirofluorene, derivatives thereof, organic metal complexes such as tris(8-quinolinolate)aluminum, triarylamine derivatives, styrylamine derivatives, stilbene derivatives, coumarin derivatives, pyran derivatives, oxazone derivatives, benzothiazole derivatives, benzoxazole derivatives, benzimidazole derivatives, pyrazine derivatives, cinnamate derivatives, diketopyrrolopyrrole derivatives, acridone derivatives, quinacridone derivatives, and the like.

The hole-injecting material is preferably a compound that can transport holes, exhibits an excellent hole-injecting effect (from the anode or to the emitting layer or the emitting material), and exhibits an excellent thin film-forming ability. Specific examples of the hole-injecting material include, but are not limited to, phthalocyanine derivatives, naphthalocyanine derivatives, porphyrin derivatives, benzidine-type triphenylamines, diamine-type triphenylamines, hexacyanohexaazatriphenylene, derivatives thereof, and polymer materials such as polyvinylcarbazoles, polysilanes, and conductive polymers.

A phthalocyanine derivative is a more effective hole-injecting material that may be used for the organic EL device according to the invention.

Examples of the phthalocyanine (Pc) derivative include, but are not limited to, phthalocyanine derivatives such as H2Pc, CuPc, CoPc, NiPc, ZnPc, PdPc, FePc, MnPc, ClAlPc, ClGaPc, ClInPc, ClSnPc, Cl2SiPc, (HO)AlPc, (HO)GaPc, VOPc, TiOPc, MoOPc, and GaPc-O-GaPc and naphthalocyanine derivatives.

It is possible to sensitize carriers by adding an electron-accepting substance (e.g., TCNQ derivative) to the hole-injecting material.

An aromatic tertiary amine derivative is a preferable hole-transporting material that may be used for the organic EL device according to the invention.

Examples of the aromatic tertiary amine derivative include N,N'-diphenyl-N,N'-dinaphthyl-1,1'-biphenyl-4,4'-diamine, N,N,N',N'-tetrabiphenyl-1,1'-biphenyl-4,4'-diamine, and oligomers or polymers that include such an aromatic tertiary amine skeleton.

The electron-injecting material is preferably a compound that can transport electrons, exhibits an excellent electron-injecting effect (from the cathode or to the emitting layer or the emitting material), and exhibits an excellent thin film-forming ability.

A metal complex compound and a nitrogen-containing heterocyclic derivative are more effective electron-injecting materials that may be used for the organic EL device according to the invention.

Examples of the metal complex compound include, but are not limited to, 8-hydroxyquinolinatolithium, bis(8-hydroxyquinolinato)zinc, tris(8-hydroxyquinolinato)aluminium, tris(8-hydroxyquinolinato)gallium, bis(10-hydroxybenzo[h]quinolinato)beryllium, bis(10-hydroxybenzo[h]quinolinato)zinc, and the like.

Examples of a preferable nitrogen-containing heterocyclic derivative include oxazole, thiazole, oxadiazole, thiadiazole, triazole, pyridine, pyrimidine, triazine, phenanthroline, benzimidazole, imidazopyridine, and the like. Among these, benzimidazole derivatives, phenanthroline derivatives, and imidazopyridine derivatives are preferable.

It is preferable that the electron-injecting material include a dopant. It is more preferable that the electron-injecting material be doped with a dopant such as an alkali metal near the cathode-side interface of the second organic layer in order to facilitate reception of electrons from the cathode.

Examples of the dopant include donor metals, donor metal compounds, and donor metal complexes. These reducing dopants may be used either independently or in combination.

In the organic electroluminescence device according to the invention, the emitting layer may include at least one of the emitting material, the dopant material, the hole-injecting material, the hole-transporting material, and the electron-injecting material in addition to at least one aromatic amine derivative shown by the formula (1). A protective layer may be provided on the surface of the organic electroluminescence device according to the invention, or the entire organic electroluminescence device may be protected with silicon oil, a resin, or the like so that the organic electroluminescence device exhibits improved stability against temperature, humidity, atmosphere, and the like.

A conductive material having a work function of larger than 4 eV is suitable as the conductive material used for the anode included in the organic EL device according to the invention. Carbon, aluminum, vanadium, iron, cobalt, nickel, tungsten, silver, gold, platinum, palladium, an alloy thereof, a metal oxide such as tin oxide or indium oxide used for an ITO substrate or an NESA substrate, or an organic conductive resin such as polythiophene or polypyrrole may be used as the conductive material used for the anode. A conductive material having a work function of smaller than 4 eV is suitable as the conductive material used for the cathode. Magnesium, calcium, tin, lead, titanium, yttrium, lithium, ruthenium, manganese, aluminum, lithium fluoride, or an alloy thereof may be used as the conductive material used for the cathode. Note that the conductive material is not limited thereto. Examples of the alloy include, but are not limited to, a magnesium/silver alloy, a magnesium/indium alloy, a lithium/aluminum alloy, and the like. The alloy ratio may be appropriately selected depending on the temperature of the deposition source, the atmosphere, the degree of vacuum, and the like. The anode and the cathode may optionally include two or more layers.

It is desirable that at least one side of the organic EL device according to the invention be sufficiently transparent within the emission wavelength range of the device so that the device efficiently emits light. It is desirable that the substrate also be transparent. A transparent electrode is formed by deposition, sputtering, or the like using the above conductive material so that a given translucency is achieved. It is desirable that the emitting-side electrode have a light transmittance of 10% or more. The substrate is not limited as long as the substrate exhibits mechanical strength and thermal strength, and has transparency. Examples of the substrate include a glass substrate and a transparent resin film.

Each layer of the organic EL device according to the invention may be formed by a dry film-forming method such as vacuum deposition, sputtering, a plasma method, or ion plating, or a wet film-forming method such as spin coating, dip coating, casting, or flow coating. The thickness of each layer is not particularly limited as long as each layer has an appropriate thickness. If the thickness of each layer is too large, a high applied voltage may be required to obtain constant optical output, so that the efficiency may deteriorate. If the thickness of each layer is too small, pinholes or the like may occur, so that sufficient luminance may not be obtained even if an electric field is applied. The thickness of each layer is normally 5 nm to 10 μm, and preferably 10 nm to 0.2 μm.

When using a wet film-forming method, the material for each layer is dissolved or dispersed in an appropriate solvent (e.g., ethanol, chloroform, tetrahydrofuran, or dioxane), and a thin film is formed using the solution. The solvent is not particularly limited.

An organic EL material-containing solution that contains the aromatic amine derivative according to the invention (i.e., organic EL material) and a solvent may be used as a solution suitable for the wet film-forming method.

It is preferable that the organic EL material include a host material and a dopant material, the dopant material be the aromatic amine derivative according to the invention, and the host material be at least one compound shown by the formula (5).

An appropriate resin or additive may be added to each organic thin film layer in order to improve the film-forming capability and prevent occurrence of pinholes, for example.

EXAMPLES

Production of Aromatic Amine Derivative

Example 1

An aromatic amine derivative D-1 was produced in accordance with the following synthesis scheme.

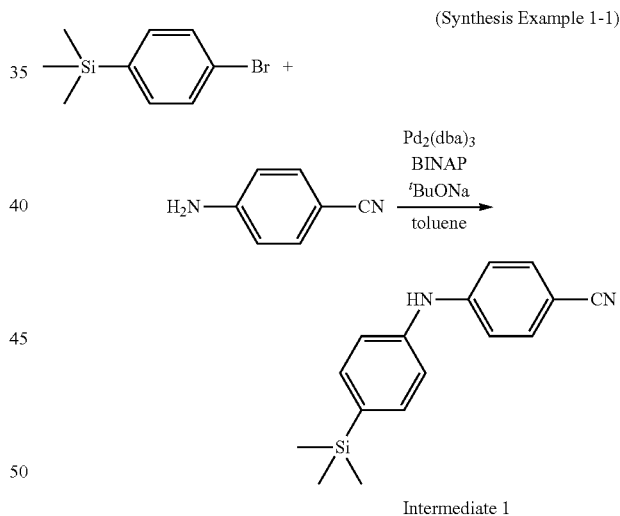

Intermediate 1

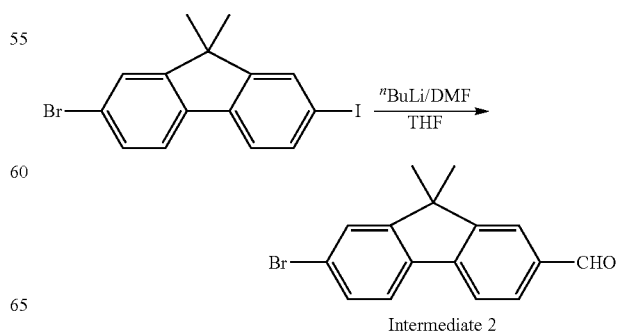

Intermediate 2

(Synthesis Example 1-3)

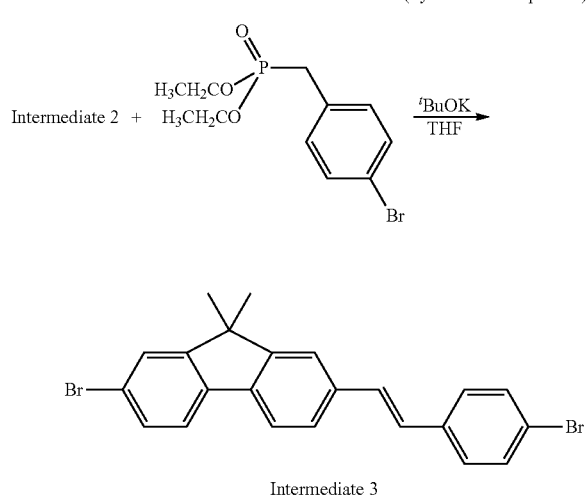

Intermediate 3

(Synthesis Example 1-4)

Intermediate 1 + Intermediate 3 $\xrightarrow[\text{toluene}]{\substack{\text{Pd}_2(\text{dba})_3 \\ \text{P}(^t\text{Bu})_3 \\ ^t\text{BuONa}}}$

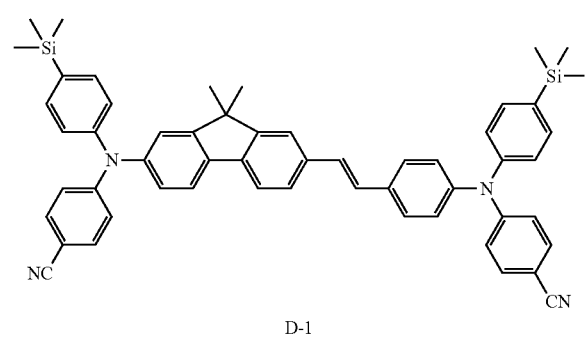

D-1

Synthesis of Intermediate 1 (Synthesis Example (1-1))

A recovery flask (2000 ml) was charged with 2.2 g of tris(dibenzylideneacetone)dipalladium(0) (Pd$_2$(dba)$_3$), 2.9 g of 2,2'-bis(diphenylphosphino)-1,1'-binaphthyl (BINAP), 36 g of 1-bromo-4-(trimethylsilyl)benzene, 37 g of 4-aminobenzonitrile, 30 g of sodium t-butoxide, and toluene under an argon stream. The mixture was stirred at 105° C. for 9 hours. The reaction solution was cooled, and filtered using celite. The filtrate was concentrated, purified by silica gel column chromatography, and dried under reduced pressure to obtain 24 g of a white solid.

The white solid was identified as the intermediate 1 by field desorption mass spectrometry (FD-MS) analysis.

Synthesis of Intermediate 2 (Synthesis Example (1-2))

A recovery flask (1000 ml) was charged with 41.9 g of 2-bromo-7-iodo-9,9-dimethylfluorene and 300 ml of dehydrated THF under an argon stream. After cooling the mixture to −65° C., 72 ml of a hexane solution (1.6 M) of n-butyllithium was added to the mixture. The mixture was stirred for 30 minutes. After the dropwise addition of 25 ml of dehydrated N,N-dimethylformamide, the mixture was slowly heated, and stirred at room temperature for 4 hours.

The mixture was separated and extracted by adding 4N hydrochloric acid and toluene. The organic layer was washed with water and a saturated sodium chloride solution, dried over sodium sulfate, and concentrated to obtain a crude product. The crude product was purified by silica gel chromatography (toluene), and the resulting solid was dried under reduced pressure to obtain 24.4 g of a white solid.

The white solid was identified as the intermediate 2 by FD-MS analysis.

Synthesis of Intermediate 3 (Synthesis Example (1-3))

A recovery flask (300 ml) was charged with 8.40 g of diethyl (4-bromobenzyl)phosphonate and 50 ml of THF under an argon stream. After cooling the mixture to −68° C., 6.16 g of potassium tert-butoxide was added to the mixture. The mixture was stirred for 90 minutes. After the dropwise addition of a THF (60 ml) solution of 6.90 g of the intermediate 2, the mixture was reacted for 2 hours, heated to room temperature with stirring over 1 hour, and stirred at room temperature for 2 hours.

The mixture was separated by adding water, and the aqueous layer was extracted with toluene. The organic layer was washed with water and a saturated sodium chloride solution, dried over sodium sulfate, and concentrated to obtain a solid. The solid was recrystallized from toluene, and the resulting solid was dried under reduced pressure to obtain 7.00 g of a yellowish-white solid. The yellowish-white solid was identified as the intermediate 3 by FD-MS analysis.

Synthesis of Compound D-1 (Synthesis Example (1-4))

A recovery flask (300 ml) was charged with 14.1 g of the intermediate 1, 10.0 g of the intermediate 3, 4.25 g of sodium tert-butoxide, 607 mg of tris(dibenzylideneacetone)dipalladium(0) (Pd$_2$(dba)$_3$), 447 mg of tri-tert-butylphosphine, and toluene under an argon stream. The mixture was stirred at 95° C. for 8 hours. The reaction solution was cooled, and filtered using celite. The filtrate was concentrated, and the resulting crude product was purified by silica gel column chromatography (toluene). The resulting amorphous solid was recrystallized three times from a toluene/methanol mixture, and dried under reduced pressure to obtain 8.6 g of a yellowish-white solid (D-1).

The FD-MS analysis results, the UV absorption maximum wavelength λmax (in toluene solution), and the fluorescence maximum wavelength of the yellowish-white solid are shown below.

FDMS, calcd for C$_{55}$H$_{52}$N$_4$Si$_2$=824, found m/z=824 (M+)
UV (PhMe): λmax, 393 nm
FL (PhMe, λex=360 nm): λmax, 435 nm

Example 2

An aromatic amine derivative D-2 was produced in accordance with the following synthesis scheme.

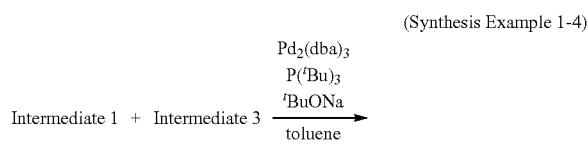

Synthesis Example (2-1)

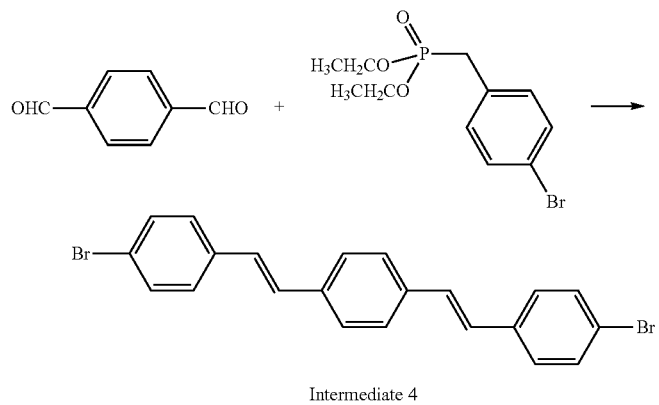

Intermediate 4

Synthesis Example (2-2)

Intermediate 1 + Intermediate 4 ⟶

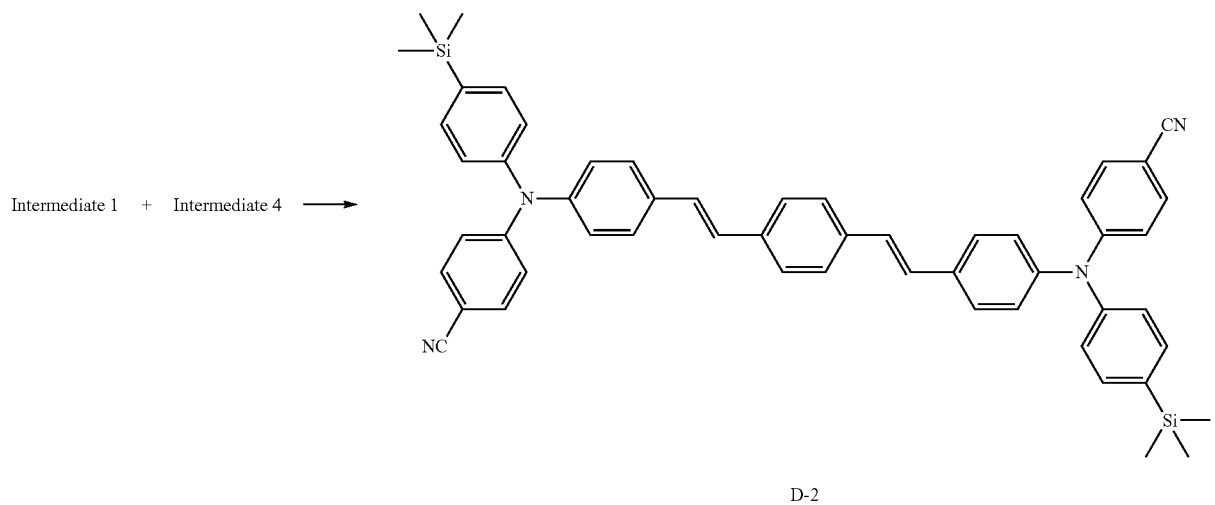

D-2

Synthesis of Intermediate 4 (Synthesis Example (2-1))

A solid was synthesized in the same manner as in synthesis of Intermediate 3, except that terephthalaldehyde was used instead of the intermediate 2. The solid was identified as the intermediate 4 by FD-MS analysis.

Synthesis of Compound D-2 (Synthesis Example (2-2))

The compound D-2 was synthesized in the same manner as the compound D-1, except that the intermediate 4 was used instead of the intermediate 3. The FD-MS analysis results, the UV absorption maximum wavelength λmax (in toluene solution), and the fluorescence maximum wavelength of the compound are shown below.

FDMS, calcd for $C_{54}H_{50}N_4Si_2$=810, found m/z=810 (M+)
UV (PhMe): λmax, 404 nm
FL (PhMe, λex=380 nm): λmax, 450 nm

Example 3

An aromatic amine derivative D-3 was produced in accordance with the following synthesis scheme.

(Synthesis Example 3-1)

Intermediate 1 +

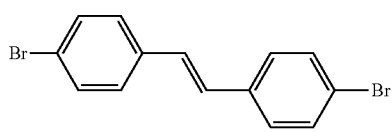

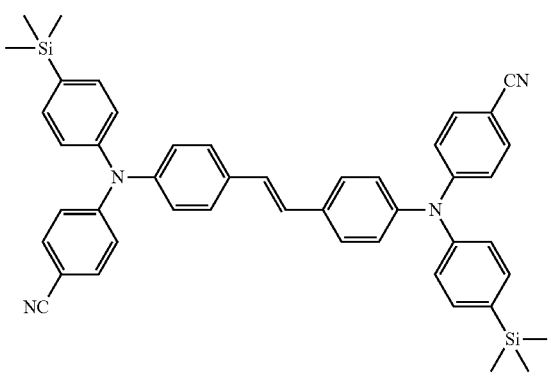

D-3

Synthesis of Compound D-3 (Synthesis Example (3-1))

The compound D-3 was synthesized in the same manner as the compound D-1, except that 4,4'-dibromostilbene was used instead of the intermediate 3. The FD-MS analysis results, the UV absorption maximum wavelength λmax (in toluene solution), and the fluorescence maximum wavelength of the compound are shown below.

FDMS, calcd for $C_{46}H_{44}N_4Si_2$=708, found m/z=708 (M+)

UV (PhMe): vmax, 386 nm

FL (PhMe, λex=360 nm): λmax, 429 nm

Example 4

An aromatic amine derivative D-4 was produced in accordance with the following synthesis scheme.

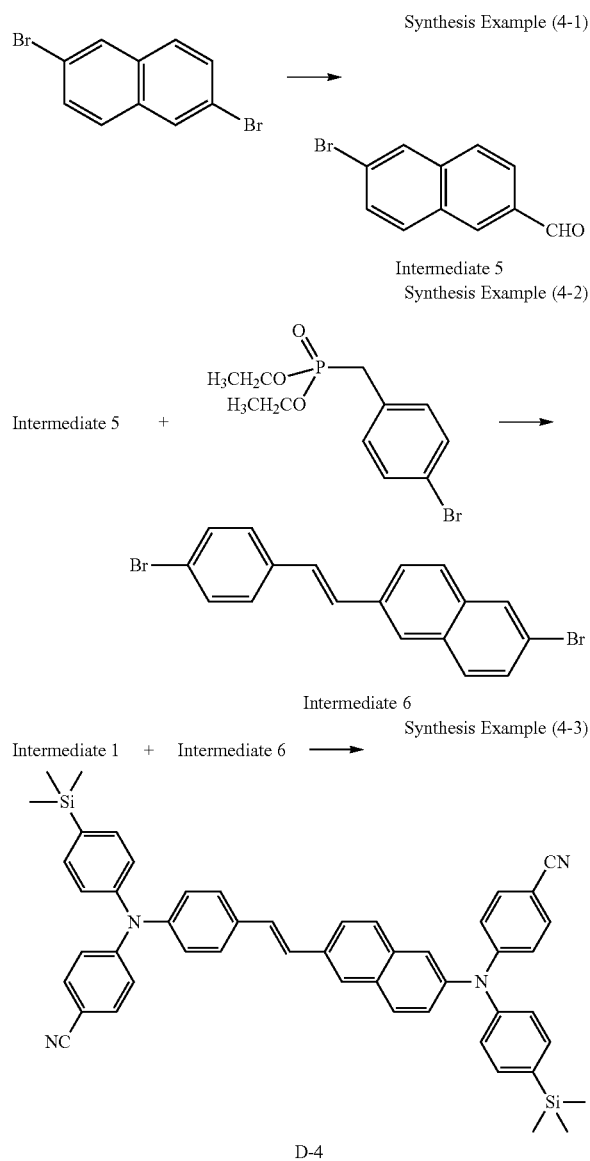

Synthesis of Intermediate 5 (Synthesis Example (4-1))

A solid was synthesized in the same manner as the intermediate 2, except that 2,6-dibromonaphthalene was used instead of 2-bromo-7-iodo-9,9-dimethylfluorene. The solid was identified as the intermediate 5 by FD-MS analysis.

Synthesis of Intermediate 6 (Synthesis Example (4-2))

A solid was synthesized in the same manner as the intermediate 3, except that the intermediate 5 was used instead of the intermediate 2.

The solid was identified as the intermediate 6 by FD-MS analysis.

Synthesis of Compound D-4 (Synthesis Example (4-3))

The compound D-4 was synthesized in the same manner as the compound D-1, except that the intermediate 6 was used instead of the intermediate 3. The FD-MS analysis results, the UV absorption maximum wavelength λmax (in toluene solution), and the fluorescence maximum wavelength of the compound are shown below.

FDMS, calcd for $C_{50}H_{46}N_4Si_2$=758, found m/z=758 (M+)

UV (PhMe): λmax, 389 nm

FL (PhMe, λex=360 nm): λmax, 428 nm

Example 5

An aromatic amine derivative D-5 was produced in accordance with the following synthesis scheme.

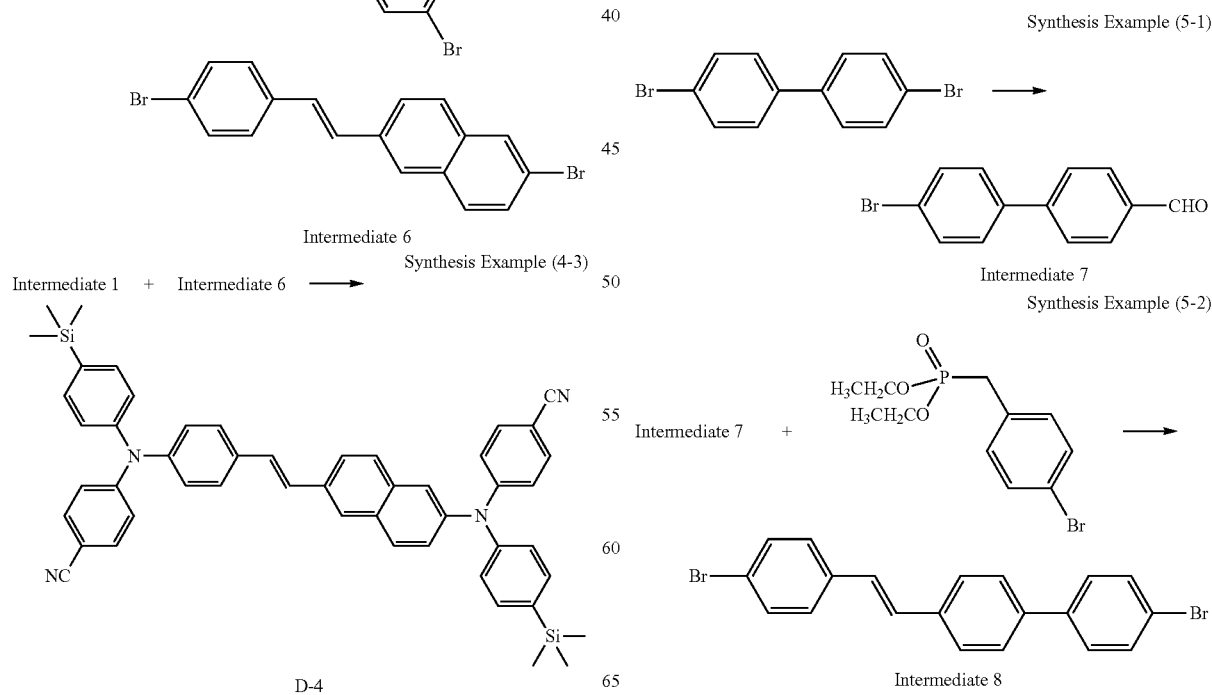

Synthesis Example (5-3)

Intermediate 1 + Intermediate 8 →

D-5

Synthesis of Intermediate 7 (Synthesis Example (5-1))

A solid was synthesized in the same manner as the intermediate 2, except that 4,4'-dibromobiphenyl was used instead of 2-bromo-7-iodo-9,9-dimethylfluorene. The solid was identified as the intermediate 7 by FD-MS analysis.

Synthesis of Intermediate 8 (Synthesis Example (5-2))

A solid was synthesized in the same manner as the intermediate 3, except that the intermediate 7 was used instead of the intermediate 2. The solid was identified as the intermediate 8 by FD-MS analysis.

Synthesis of Compound D-5 (Synthesis Example (5-3))

The compound D-5 was synthesized in the same manner as the compound D-1, except that the intermediate 8 was used instead of the intermediate 3. The FD-MS analysis results, the UV absorption maximum wavelength λmax (in toluene solution), and the fluorescence maximum wavelength of the compound are shown below.

FDMS, calcd for $C_{52}H_{48}N_4Si_2$=784, found m/z=784 (M+)
UV (PhMe): λmax, 431 nm
FL (PhMe, λex=350 nm): λmax, 373 nm

Example 6

An aromatic amine derivative D-6 was produced in accordance with the following synthesis scheme.

Synthesis Example (6-1)

Intermediate 9

Synthesis Example (6-2)

Intermediate 9 +

D-6

Synthesis of Intermediate 9 (Synthesis Example (6-1))

A solid was synthesized in the same manner as the intermediate 1, except that 1-bromo-4-tert-butylbenzene was used instead of 1-bromo-4-(trimethylsilyl)benzene. The solid was identified as the intermediate 9 by FD-MS analysis.

Synthesis of Compound D-6 (Synthesis Example (6-2))

The compound D-6 was synthesized in the same manner as the compound D-1, except that the intermediate 9 was used instead of the intermediate 1, and 4,4'-dibromostilbene was used instead of the intermediate 3. The FD-MS analysis results, the UV absorption maximum wavelength λmax (in toluene solution), and the fluorescence maximum wavelength of the compound are shown below.

FDMS, calcd for $C_{48}H_{44}N_4$=676, found m/z=676 (M+)
UV (PhMe): λmax, 389 nm
FL (PhMe, λex=360 nm): λmax, 432 nm

Example 7

An aromatic amine derivative D-7 was produced in accordance with the following synthesis scheme.

Synthesis Example (7-1)

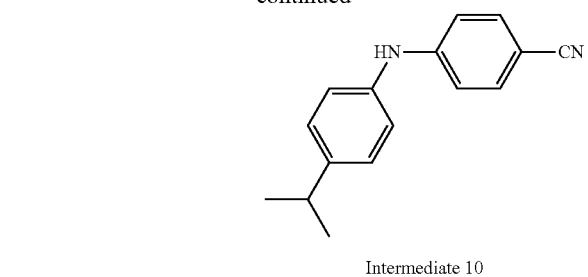

Intermediate 10

Synthesis Example (7-2)

Intermediate 10 +

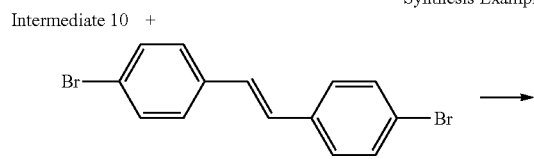

D-7

Synthesis Example (8-1)

Intermediate 10 + Intermediate 3 ⟶

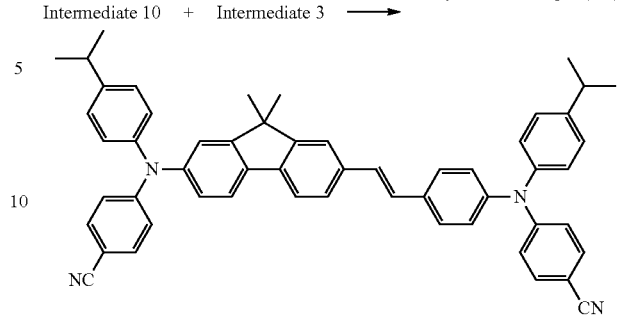

D-8

Synthesis of Compound D-8 (Synthesis Example (8-1))

The compound D-8 was synthesized in the same manner as the compound D-1, except that the intermediate 10 was used instead of the intermediate 1. The FD-MS analysis results, the UV absorption maximum wavelength λmax (in toluene solution), and the fluorescence maximum wavelength of the compound are shown below.

FDMS, calcd for $C_{55}H_{48}N_4$=764, found m/z=764 (M+)

UV (PhMe): λmax, 395 nm

FL (PhMe, λex=370 nm): λmax, 437 nm

Example 9

An aromatic amine derivative D-9 was produced in accordance with the following synthesis scheme.

Synthesis of Intermediate 10 (Synthesis Example (7-1))

A solid was synthesized in the same manner as the intermediate 1, except that 1-bromo-4-isopropylbenzene was used instead of 1-bromo-4-(trimethylsilyl)benzene. The solid was identified as the intermediate 10 by FD-MS analysis.

Synthesis of Compound D-7 (Synthesis Example (7-2))

The compound D-7 was synthesized in the same manner as the compound D-1, except that the intermediate 10 was used instead of the intermediate 1, and 4,4'-dibromostilbene was used instead of the intermediate 3. The FD-MS analysis results, the UV absorption maximum wavelength λmax (in toluene solution), and the fluorescence maximum wavelength of the compound are shown below.

FDMS, calcd for $C_{46}H_{40}N_4$=648, found m/z=648 (M+)

UV (PhMe): λmax, 387 nm

FL (PhMe, λex=360 nm): λmax, 431 nm

Example 8

An aromatic amine derivative D-8 was produced in accordance with the following synthesis scheme.

Synthesis Example (9-1)

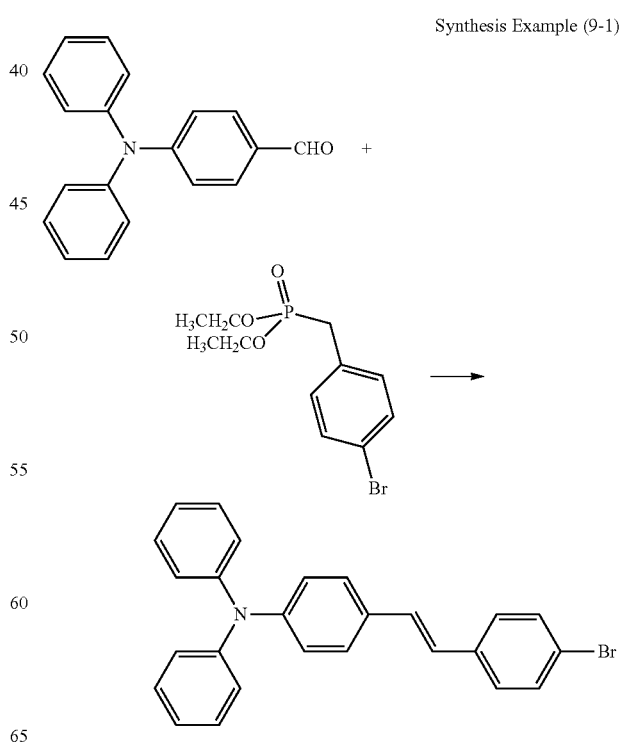

Intermediate 11

-continued

Synthesis Example (9-2)

Intermediate 1 + Intermediate 11 ⟶

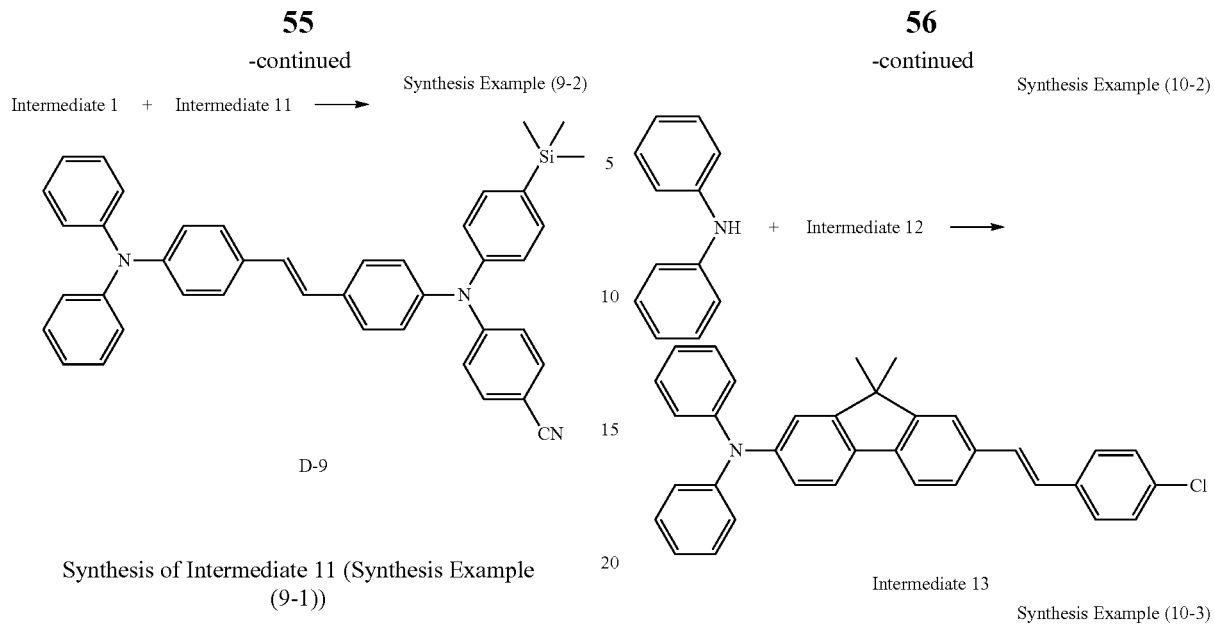

D-9

Synthesis of Intermediate 11 (Synthesis Example (9-1))

A solid was synthesized in the same manner as the intermediate 3, except that 4-(N,N-diphenylamino)benzaldehyde was used instead of the intermediate 2. The solid was identified as the intermediate 11 by FD-MS analysis.

Synthesis of Compound D-9 (Synthesis Example (9-2))

The compound D-9 was synthesized in the same manner as the compound D-1, except that the intermediate 11 was used instead of the intermediate 3. The FD-MS analysis results, the UV absorption maximum wavelength λmax (in toluene solution), and the fluorescence maximum wavelength of the compound are shown below.

FDMS, calcd for $C_{42}H_{37}N_3Si=611$, found m/z=611 (M+)

UV (PhMe): λmax, 389 nm

FL (PhMe, λex=360 nm): λmax, 432 nm

Example 10

An aromatic amine derivative D-10 was produced in accordance with the following synthesis scheme.

Synthesis Example (10-1)

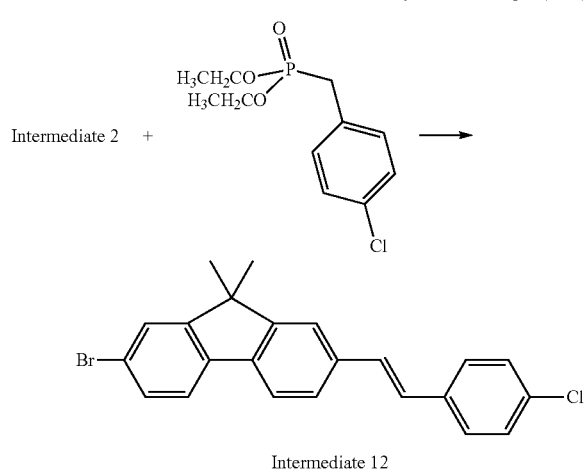

Intermediate 12

-continued

Synthesis Example (10-2)

Intermediate 13

Synthesis Example (10-3)

Intermediate 1 + Intermediate 13 ⟶

D-10

Synthesis of Intermediate 12 (Synthesis Example (10-1))

A solid was synthesized in the same manner as the intermediate 3, except that diethyl (4-chlorobenzyl)phosphonate was used instead of diethyl (4-bromobenzyl)phosphonate. The solid was identified as the intermediate 12 by FD-MS analysis.

Synthesis of Intermediate 13 (Synthesis Example (10-2))

A solid was synthesized in the same manner as the compound D-1, except that the intermediate 12 was used instead of the intermediate 3, and diphenylamine was used instead of the intermediate 1. The solid was identified as the intermediate 13 by FD-MS analysis.

Synthesis of Compound D-10 (Synthesis Example (10-3))

The compound D-10 was synthesized in the same manner as the compound D-1, except that the intermediate 13 was used instead of the intermediate 3. The FD-MS analysis results, the UV absorption maximum wavelength λmax (in toluene solution), and the fluorescence maximum wavelength of the compound are shown below.

FDMS, calcd for $C_{51}H_{45}N_3Si=727$, found m/z=727 (M+)

UV (PhMe): λmax, 397 nm

FL (PhMe, λex=370 nm): λmax, 441 nm

Example 11

An aromatic amine derivative D-11 was produced in accordance with the following synthesis scheme.

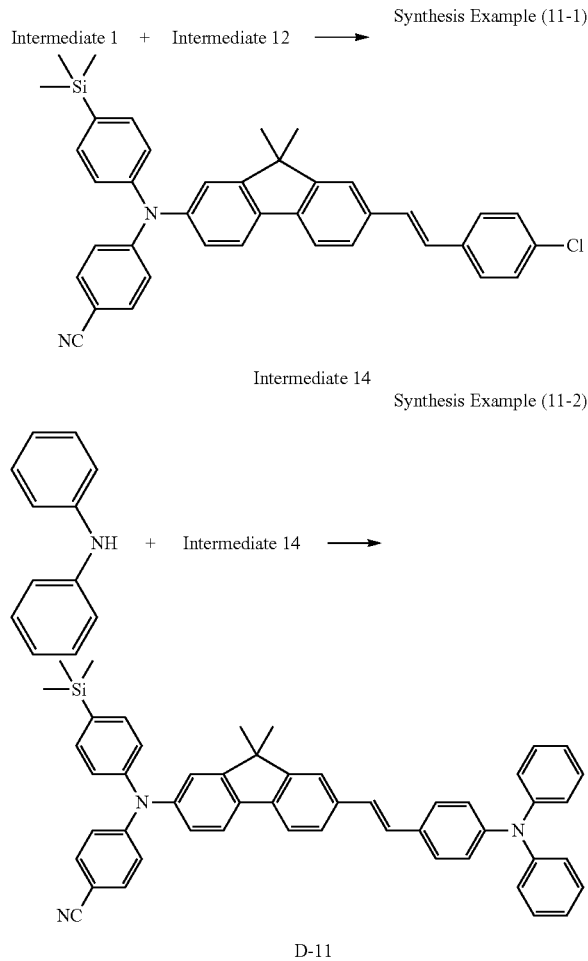

Synthesis of Intermediate 14 (Synthesis Example (11-1))

A solid was synthesized in the same manner as the compound D-1, except that the intermediate 12 was used instead of the intermediate 3. The solid was identified as the intermediate 14 by FD-MS analysis.

Synthesis of Compound D-11 (Synthesis Example (11-2))

The compound D-11 was synthesized in the same manner as the compound D-1, except that the intermediate 14 was used instead of the intermediate 3, and diphenylamine was used instead of the intermediate 1. The FD-MS analysis results, the UV absorption maximum wavelength λmax (in toluene solution), and the fluorescence maximum wavelength of the compound are shown below.

FDMS, calcd for $C_{51}H_{45}N_3Si$=727, found m/z=727 (M+)
UV (PhMe): λmax, 396 nm
FL (PhMe, λex=370 nm): λmax, 440 nm

Fabrication of Organic EL Device

Example 12

A transparent electrode (thickness: 120 nm) was formed on a glass substrate (25×75×1.1 mm) using indium tin oxide. The transparent electrode functions as an anode. The glass substrate was cleaned by applying ultraviolet rays and ozone, and placed in a vacuum deposition apparatus.

A compound HT-1 was deposited on the anode to a thickness of 50 nm to form a hole-injecting layer. N,N,N',N'-tetrakis(4-biphenyl)-4,4'-benzidine was deposited on the hole-injecting layer to a thickness of 45 nm to form a hole-transporting layer. An anthracene derivative BH-1 (host material) and the compound D-1 (dopant material) were codeposited on the hole-transporting layer in a mass ratio of 25:5 to form an emitting layer having a thickness of 30 nm. A compound ET-1 was deposited on the emitting layer to a thickness of 25 nm to form an electron-injecting layer. After depositing lithium fluoride to a thickness of 1 nm, aluminum was deposited to a thickness of 150 nm. An organic EL device was thus fabricated. Note that the aluminum/lithium fluoride film functions as a cathode.

The compounds HT-1, ET-1, BH-1, and BH-2 used to fabricate the organic EL device respectively had the following structures.

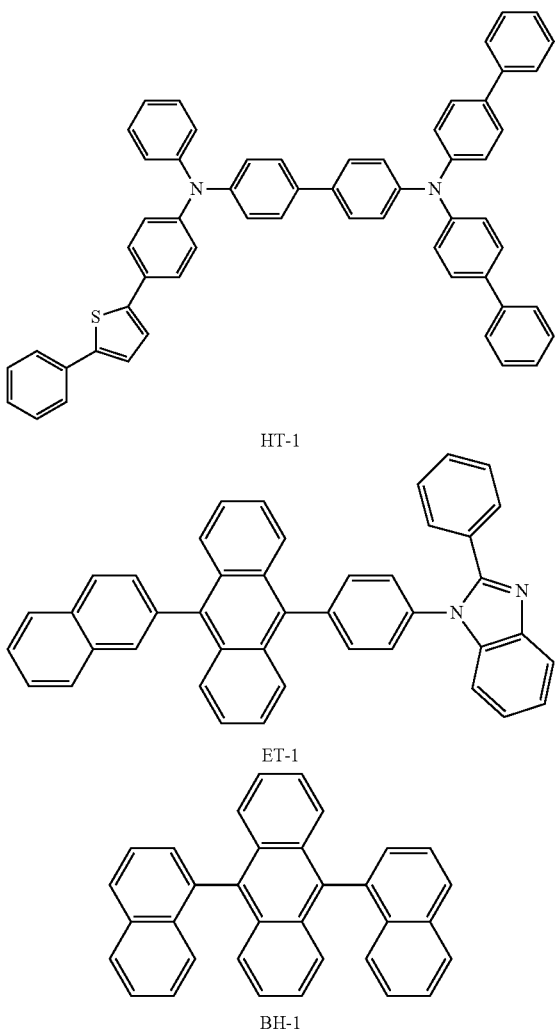

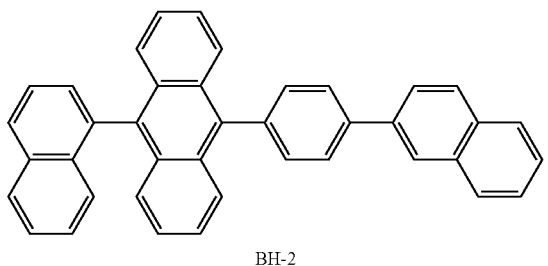

BH-2

The device performance (drive voltage) at a current density of 10 mA/cm², x and y in the CIE 1931 chromaticity diagram, and the half life were evaluated using the organic EL device. The results are shown in Table 1.

Examples 13 to 22 and Comparative Examples 1 to 3

An organic EL device was fabricated and evaluated in the same manner as in Example 12, except that the compounds shown in Table 1 were used as the host material and the dopant material. The results are shown in Table 1.

The compounds H-1, H-2, and H-3 respectively had the following structures.

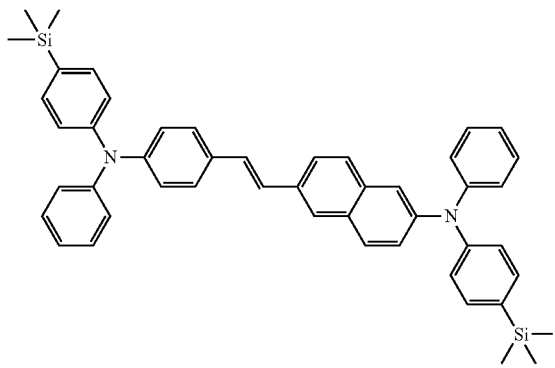
H-1

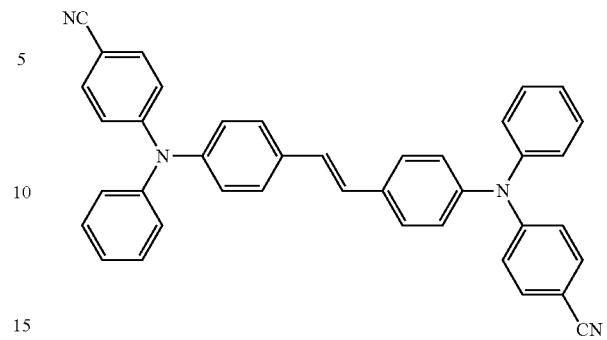

TABLE 1

| | Host material | Doping material | Voltage [V] | CIEx | CIEy | Lifetime [h] |
|---|---|---|---|---|---|---|
| Example 12 | BH-1 | D-1 | 3.1 | 0.149 | 0.094 | 600 |
| Example 13 | BH-1 | D-2 | 3.1 | 0.151 | 0.188 | 700 |
| Example 14 | BH-2 | D-3 | 3.1 | 0.150 | 0.068 | 400 |
| Example 15 | BH-2 | D-4 | 3.1 | 0.148 | 0.088 | 400 |
| Example 16 | BH-1 | D-5 | 3.1 | 0.148 | 0.080 | 400 |
| Example 17 | BH-1 | D-6 | 3.1 | 0.149 | 0.075 | 420 |
| Example 18 | BH-1 | D-7 | 3.1 | 0.151 | 0.078 | 430 |
| Example 19 | BH-1 | D-8 | 3.1 | 0.146 | 0.106 | 580 |
| Example 20 | BH-1 | D-9 | 3.2 | 0.149 | 0.090 | 400 |
| Example 21 | BH-1 | D-10 | 3.2 | 0.144 | 0.131 | 600 |
| Example 22 | BH-1 | D-11 | 3.2 | 0.144 | 0.130 | 600 |
| Comparative Example 1 | BH-1 | H-1 | 3.4 | 0.148 | 0.135 | 200 |
| Comparative Example 2 | BH-1 | H-2 | 3.5 | 0.148 | 0.132 | 250 |
| Comparative Example 3 | BH-1 | H-3 | 3.5 | 0.148 | 0.066 | 80 |

As is clear from the results shown in Table 1, an organic EL device that can be driven at a low voltage within a practical high current region was implemented by utilizing the aromatic amine derivative according to the invention. When using the compound H-1 that did not contain a cyano group, or the compound H-3 that did not contain a substituted silyl group, an alkyl group, or a cycloalkyl group, the drive voltage of the organic EL device increased as compared with the case of using the aromatic amine derivative according to the invention.

It is considered that the organic EL device fabricated using the aromatic amine derivative according to the invention had a long lifetime due to an improvement in carrier injection capability.

INDUSTRIAL APPLICABILITY

The organic EL device according to the invention may be used as a planar emitting device (e.g., a flat panel display of a wall TV), a backlight of a copier, a printer, or a liquid crystal display, a light source of an instrument (meter), a signboard, a marker lamp (light), and the like. The compound according to the invention may also be used in the fields of electrophotographic photoreceptors, photoelectric conversion devices, solar cells, image sensors, and the like in addition to the organic EL device.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in their entirety.

The invention claimed is:

1. A compound of formula (1):

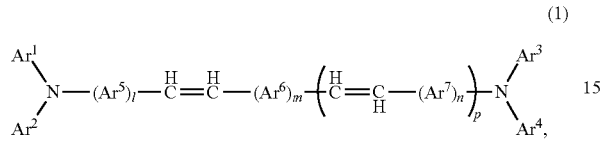

wherein
p is 0, l is 1, m is 1, and Ar⁶ and N are bonded via a single bond,
$Ar^1$ to $Ar^4$ are each independently a substituted aryl group comprising 6 to 30 ring carbon atoms,
$Ar^5$ and $Ar^6$ are each independently a substituted or unsubstituted arylene group comprising 6 to 30 ring carbon atoms, or a substituted or unsubstituted heteroarylene group comprising 5 to 30 ring atoms, and
two of $Ar^1$ to $Ar^4$ are each independently substituted with a substituted silyl group, a substituted or unsubstituted alkyl group comprising 1 to 20 carbon atoms, or a substituted or unsubstituted cycloalkyl group comprising 3 to 10 carbon atoms, and the remainder of $Ar^1$ to $Ar^4$ are each independently substituted with a cyano group.

2. The compound of claim 1, wherein $Ar^1$ and $Ar^4$ are each independently an aryl group comprising 6 to 30 ring carbon atoms that is substituted with a substituted silyl group, a substituted or unsubstituted alkyl group comprising 1 to 20 carbon atoms, or a substituted or unsubstituted cycloalkyl group comprising 3 to 10 carbon atoms, and
$Ar^2$ and $Ar^3$ are each independently an aryl group comprising 6 to 30 ring carbon atoms that is substituted with a cyano group.

3. The compound of claim 1, wherein $Ar^1$ and $Ar^4$ are each independently a phenyl group that is substituted with a substituted silyl group, a substituted or unsubstituted alkyl group comprising 1 to 20 carbon atoms, or a substituted or unsubstituted cycloalkyl group comprising 3 to 10 carbon atoms, and
$Ar^2$ and $Ar^3$ are each independently a phenyl group that is substituted with a cyano group.

4. The compound of claim 1, wherein $Ar^5$ and $Ar^6$ are each independently a substituted or unsubstituted arylene group comprising 6 to 30 ring carbon atoms.

5. The compound of claim 1, wherein $Ar^5$ and $Ar^6$ are each independently a substituted or unsubstituted phenylene group, a substituted or unsubstituted naphthylene group, a substituted or unsubstituted biphenylene group, or a substituted or unsubstituted fluorenylene group.

6. An organic electroluminescence device, comprising:
a cathode;
an anode; and
an organic thin film layer comprising at least an emitting layer,
wherein the organic thin film layer is between the cathode and the anode, and comprises the compound of claim 1.

7. The device of claim 6, wherein the organic thin film layer is the emitting layer.

8. The device of claim 6, wherein the organic thin film layer further comprises an anthracene derivative of formula (5):

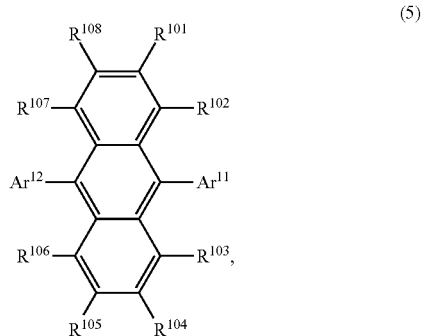

wherein
$Ar^{11}$ and $Ar^{12}$ are each independently a substituted or unsubstituted monocyclic group comprising 5 to 50 ring atoms, a substituted or unsubstituted fused cyclic group comprising 8 to 50 ring atoms, or a combination of a substituted or unsubstituted monocyclic group comprising 5 to 50 ring atoms and a substituted or unsubstituted fused cyclic group comprising 8 to 50 ring atoms, and
$R^{101}$ to $R^{108}$ are each independently a group selected from a hydrogen atom, a substituted or unsubstituted monocyclic group comprising 5 to 50 ring atoms, a substituted or unsubstituted fused cyclic group comprising 8 to 50 ring atoms, a combination of a substituted or unsubstituted monocyclic group comprising 5 to 50 ring atoms and a substituted or unsubstituted fused cyclic group comprising 8 to 50 ring atoms, a substituted or unsubstituted alkyl group comprising 1 to 50 carbon atoms, a substituted or unsubstituted cycloalkyl group comprising 3 to 50 ring carbon atoms, a substituted or unsubstituted alkoxy group comprising 1 to 50 carbon atoms, a substituted or unsubstituted aralkyl group comprising 7 to 50 carbon atoms, a substituted or unsubstituted aryloxy group comprising 6 to 50 ring carbon atoms, a substituted or unsubstituted silyl group, a halogen atom, or a cyano group.

9. A compound of formula (21):

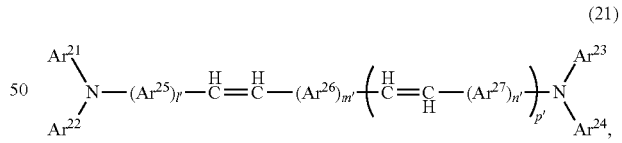

wherein
p' is 0, l' is 1, m' is 1, and $Ar^{26}$ and N are bonded via a single bond,
$Ar^{21}$ to $Ar^{24}$ are each independently a substituted or unsubstituted aryl group comprising 6 to 30 ring carbon atoms, or a substituted or unsubstituted heteroaryl group comprising 5 to 30 ring atoms,
$Ar^{25}$ and $Ar^{26}$ are each independently a substituted or unsubstituted phenylene group, a substituted or unsubstituted biphenylene group, or a substituted or unsubstituted fluorenylene group, and
at least one of $Ar^{21}$ to $Ar^{24}$ is substituted with a substituted silyl group, and at least one of $Ar^{21}$ to $Ar^{24}$ is substituted with a cyano group.

10. The compound of claim 9, wherein two of $Ar^{21}$ to $Ar^{24}$ are substituted with a substituent, one being substituted with a substituted silyl group, and the other being substituted with a cyano group.

11. The compound of claim 9, wherein $Ar^{21}$ to $Ar^{24}$ are each independently a substituted or unsubstituted aryl group comprising 6 to 30 ring carbon atoms.

12. An organic electroluminescence device, comprising:
    a cathode;
    an anode; and
    an organic thin film layer comprising at least an emitting layer,
    wherein the organic thin film layer is between the cathode and the anode, and comprises the compound of claim 9.

13. The device of claim 12, wherein the organic thin film layer is the emitting layer.

14. The device of claim 12, wherein the organic thin film layer further comprises an anthracene derivative of formula (5):

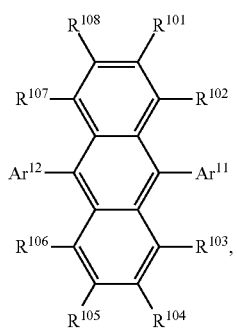

wherein
  $Ar^{11}$ and $Ar^{12}$ are each independently a substituted or unsubstituted monocyclic group comprising 5 to 50 ring atoms, a substituted or unsubstituted fused cyclic group comprising 8 to 50 ring atoms, or a combination of a substituted or unsubstituted monocyclic group comprising 5 to 50 ring atoms and a substituted or unsubstituted fused cyclic group comprising 8 to 50 ring atoms, and
  $R^{101}$ to $R^{108}$ are each independently a group selected from a hydrogen atom, a substituted or unsubstituted monocyclic group comprising 5 to 50 ring atoms, a substituted or unsubstituted fused cyclic group comprising 8 to 50 ring atoms, a combination of a substituted or unsubstituted monocyclic group comprising 5 to 50 ring atoms and a substituted or unsubstituted fused cyclic group comprising 8 to 50 ring atoms, a substituted or unsubstituted alkyl group comprising 1 to 50 carbon atoms, a substituted or unsubstituted cycloalkyl group comprising 3 to 50 ring carbon atoms, a substituted or unsubstituted alkoxy group comprising 1 to 50 carbon atoms, a substituted or unsubstituted aralkyl group comprising 7 to 50 carbon atoms, a substituted or unsubstituted aryloxy group comprising 6 to 50 ring carbon atoms, a substituted or unsubstituted silyl group, a halogen atom, or a cyano group.

15. A compound of formula (31):

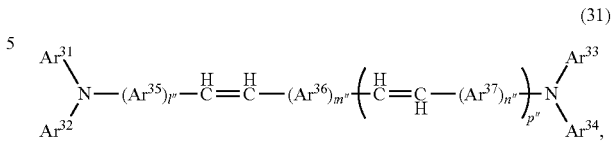

wherein
  p", l", m", and n" are each 1,
  $Ar^{31}$ to $Ar^{34}$ are each independently a substituted or unsubstituted aryl group comprising 6 to 30 ring carbon atoms, or a substituted or unsubstituted heteroaryl group comprising 5 to 30 ring atoms,
  $Ar^{35}$, $Ar^{36}$, and $Ar^{37}$ are each independently a substituted or unsubstituted phenylene group, a substituted or unsubstituted naphthylene group, or a substituted or unsubstituted biphenylene group, and
  at least one of $Ar^{31}$ to $Ar^{34}$ is substituted with a substituted silyl group, a substituted or unsubstituted alkyl group comprising 1 to 20 carbon atoms, or a substituted or unsubstituted cycloalkyl group comprising 3 to 10 carbon atoms, and at least one of $Ar^{31}$ to $Ar^{34}$ is substituted with a cyano group.

16. The compound of claim 15, wherein at least one of $Ar^{31}$ to $Ar^{34}$ is substituted with a substituted silyl group, and at least one of $Ar^{31}$ to $Ar^{34}$ is substituted with a cyano group.

17. The compound of claim 16, wherein the substituted silyl group is a substituted or unsubstituted alkylsilyl group comprising 1 to 20 carbon atoms.

18. The compound of claim 15, wherein two of $Ar^{31}$ to $Ar^{34}$ are each independently substituted with a substituted silyl group, a substituted or unsubstituted alkyl group comprising 1 to 20 carbon atoms, or a substituted or unsubstituted cycloalkyl group comprising 3 to 10 carbon atoms, and the remainder of $Ar^{31}$ to $Ar^{34}$ are each independently substituted with a cyano group.

19. The compound of claim 15, wherein $Ar^{31}$ to $Ar^{34}$ are each independently a substituted or unsubstituted aryl group comprising 6 to 30 ring carbon atoms.

20. The compound of claim 15, wherein $Ar^{31}$ and $Ar^{34}$ are each independently an aryl group comprising 6 to 30 ring carbon atoms that is substituted with a substituted silyl group, a substituted or unsubstituted alkyl group comprising 1 to 20 carbon atoms, or a substituted or unsubstituted cycloalkyl group comprising 3 to 10 carbon atoms, and
  $Ar^{32}$ and $Ar^{33}$ are each independently an aryl group comprising 6 to 30 ring carbon atoms that is substituted with a cyano group.

21. The compound of claim 15, wherein $Ar^{31}$ and $Ar34$ are each independently a phenyl group that is substituted with a substituted silyl group, a substituted or unsubstituted alkyl group comprising 1 to 20 carbon atoms, or a substituted or unsubstituted cycloalkyl group comprising 3 to 10 carbon atoms, and
  $Ar^{32}$ and $Ar^{33}$ are each independently a phenyl group that is substituted with a cyano group.

22. An organic electroluminescence device, comprising:
    a cathode;
    an anode; and
    an organic thin film layer comprising at least an emitting layer,
    wherein the organic thin film layer is between the cathode and the anode, and comprises the compound of claim 15.

23. The device of claim 22, wherein the organic thin film layer is the emitting layer.

24. The device of claim 22, wherein the organic thin film layer further comprises an anthracene derivative of formula (5):

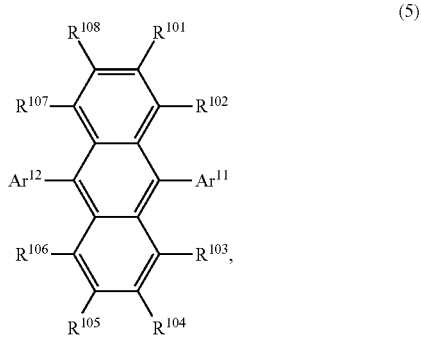

(5)

wherein

Ar$^{11}$ and Ar$^{12}$ are each independently a substituted or unsubstituted monocyclic group comprising 5 to 50 ring atoms, a substituted or unsubstituted fused cyclic group comprising 8 to 50 ring atoms, or a combination of a substituted or unsubstituted monocyclic group comprising 5 to 50 ring atoms and a substituted or unsubstituted fused cyclic group comprising 8 to 50 ring atoms, and R$^{101}$ to R$^{108}$ are each independently a group selected from a hydrogen atom, a substituted or unsubstituted monocyclic group comprising 5 to 50 ring atoms, a substituted or unsubstituted fused cyclic group comprising 8 to 50 ring atoms, a combination of a substituted or unsubstituted monocyclic group comprising 5 to 50 ring atoms and a substituted or unsubstituted fused cyclic group comprising 8 to 50 ring atoms, a substituted or unsubstituted alkyl group comprising 1 to 50 carbon atoms, a substituted or unsubstituted cycloalkyl group comprising 3 to 50 ring carbon atoms, a substituted or unsubstituted alkoxy group comprising 1 to 50 carbon atoms, a substituted or unsubstituted aralkyl group comprising 7 to 50 carbon atoms, a substituted or unsubstituted aryloxy group comprising 6 to 50 ring carbon atoms, a substituted or unsubstituted silyl group, a halogen atom, or a cyano group.

25. The compound according to claim 1, wherein Ar$^5$ and Ar$^6$ are each independently a phenylene group, a naphthylene group, an anthrylene group, a phenanthrylene group, a naphthacenylene group, a pyrenylene group, a chrysenylene group, a benzo[c]phenanthrylene group, a benzo[g]chrysenylene group, a triphenylenylene group, a benzofluorenylene group, a dibenzofluorenylene group, a biphenylene group, or a fluoranthenylene group.

* * * * *